(12) United States Patent
Knopf et al.

(10) Patent No.: US 8,293,238 B2
(45) Date of Patent: Oct. 23, 2012

(54) GDF3 ANTIBODIES AND RELATED METHODS

(75) Inventors: John Knopf, Carlisle, MA (US); Jasbir Seehra, Lexington, MA (US)

(73) Assignee: Acceleron Pharma Inc., Cambridge, MA (US)

(*) Notice: Subject to any disclaimer, the term of this patent is extended or adjusted under 35 U.S.C. 154(b) by 1275 days.

(21) Appl. No.: 11/726,461

(22) Filed: Mar. 21, 2007

(65) Prior Publication Data

US 2007/0172481 A1 Jul. 26, 2007

Related U.S. Application Data

(63) Continuation of application No. 11/165,963, filed on Jun. 24, 2005, now Pat. No. 7,465,706.

(60) Provisional application No. 60/583,073, filed on Jun. 24, 2004.

(51) Int. Cl.
*A61K 39/395* (2006.01)
*A61K 39/00* (2006.01)
*C07K 16/00* (2006.01)
*C12P 21/08* (2006.01)

(52) U.S. Cl. ............... 424/141.1; 424/133.1; 424/139.1; 424/142.1; 424/145.1; 530/388.1; 530/388.15; 530/388.24; 530/387.3; 530/387.9

(58) Field of Classification Search .................. None
See application file for complete search history.

(56) References Cited

U.S. PATENT DOCUMENTS

| | | | |
|---|---|---|---|
| 5,637,480 A | 6/1997 | Celeste | |
| 5,808,007 A | 9/1998 | Lee et al. | |
| 5,834,179 A | 11/1998 | Jones et al. | |
| 6,004,780 A | 12/1999 | Soppet et al. | |
| 6,071,708 A | 6/2000 | Jones et al. | |
| 6,656,708 B1 | 12/2003 | Yu et al. | |
| 2002/0137143 A1 | 9/2002 | Soppet et al. | |
| 2003/0082233 A1 | 5/2003 | Lyons et al. | |
| 2003/0144176 A1 | 7/2003 | Olson et al. | |
| 2003/0224501 A1* | 12/2003 | Young et al. | 435/226 |
| 2005/0244867 A1 | 11/2005 | Soppet et al. | |

FOREIGN PATENT DOCUMENTS

| | | |
|---|---|---|
| WO | WO-94/03600 A1 | 2/1994 |
| WO | WO-94/15965 A | 7/1994 |
| WO | WO-94/26893 A1 | 11/1994 |
| WO | WO-95/24474 A1 | 9/1995 |
| WO | WO-96/39431 A1 | 12/1996 |
| WO | WO-99/37320 A1 | 7/1999 |
| WO | WO-00/43781 | 7/2000 |
| WO | WO-01/922298 | 12/2001 |
| WO | WO-0192298 A2 | 12/2001 |
| WO | WO-02/43759 | 6/2002 |

OTHER PUBLICATIONS

Bork, 2000, Powers and pitfalls in sequence analysis: the 70% hurdle, Genome Res. 10:398-400.

Brenner, 1999, Errors in genome annotation, Trends in Genetics, 15(4):132-133.
Doerks et al., 1998, Protein annotation: detective work for function prediction, Trends in Genetics, 14(6):248-250.
Graddis et al., 2002, Designing proteins that work using recombinant technologies, Curr. Pharm. Biotechnol. 3:285.
Hino et al. Coordination of BMP-3b and cerberus is required for head formation of *Xenopus* embryos. Developmental Biology, 260, 138-157, available on line Jun. 4, 2003.
Kirsch et al., EMBO J., 2000, 19(13):3314-3324.
Ngo et al., 1994, Computational complexity, protein structure prediction, and the Levinthal paradox. The Protein Folding Problem and Tertiary Structure Prediction, pp. 492-495.
Skolnick et al., 2000, From genes to protein structure and function: novel applications of computational approaches in the genomic era, Trends in Biotech. 18(1):34-39.
Smith et al., 1997, The challenges of genome sequence annotation or "the devil is in the details," Nature Biotech. 15:1222-1223.
Srivastava, Nature, Jun. 2004, 429:819-822.
Wells, 1990, Additivity of mutational effects in proteins, Biochemistry 29(37):8509-8517.
Caricasole et al., "Human growth-differentiation factor 3 (hGDF3): developmental regulation in human teratocarcinoma cell lines and expression in primary testicular germ cell tumours," *Oncogene*, 16: 95-103 (1998).
Chen, H., et al., "BMP10 is essential for maintaining cardiac growth during murine cardiogenesis," Development, 131(9):2219-2231 (2004).
Clark et al., "Human STELLAR, NANOG, and GDF3 Genes are Expressed in Pluripotent Cells and Map to Chromosome 12p13, a Hotspot for Teratocarcinoma," *Stem Cells*, 22: 169-179 (2004).
Constam et al., "Regulation of Bone Morphogenetic Protein Activity by Pro Domains and Proprotein Convertases", The Journal of Cell Biology, 144(1):139-149(1999).
Daluiski et al., "Bone Morphogenetic Protein-3 is a Negative Regulatory of Bone Density", Nature Genetics, 27(1):84-88(2001).
Faucheux et al., "Opposing Actions of BMP3 and TGFbetal in Human Bone Marrow Stromal Cell Growth and Differentiation", Biochemical and Biophysical Research Communications, 241(3):787-793(1997).
Hino et al. "Bone Morphogenetic Protein-3 Family Members and Their Biological Functions," Frontiers in Bioscience, 9:1520-1529(2004). Hino et al., "Bone Morphogenetic Protein-3B (BMP-3B) Gene Expression is Correlated with Differentiation in Rat Calvarial Osteoblasts", Biochemical and Biophysical Research Communications, 256(2):419-424(1999).
Hino et al., "Coordination of BMP-3b and cerebus is required for head formation of *Xenopus* embryos", Developmental Biology, 260(1):138-157(2003).
McPherron et at., "GDF-3 and GDF-9: two new members of the transforming growth factor-beta superfamily containing a novel pattern of cysteines," *Journal of Biological Chemistry*, 268 (5): 3444-9 (1993).

(Continued)

*Primary Examiner* — Xiaozhen Xie

(74) *Attorney, Agent, or Firm* — Ropes & Gray LLP

(57) ABSTRACT

The application describes compositions and methods for regulating body weight, in particular, for treating obesity and obesity-associate disorders. The application also provides methods of screening compounds that modulate activity of GDF3. These compositions and methods are also useful in treating diseases associated with abnormal activity of GDF3.

4 Claims, 9 Drawing Sheets

OTHER PUBLICATIONS

Nagaso et al., "Dual Specificity of Activin Type II Receptor ActRIIb in Dorso-Ventral Patterning During Zebrafish Embryogenesis", Development Growth and Differentiation, 41(2)119-133(1999).

Neuhaus, H., et al., "Heart specific expression of mouse *BMP-10* a novel member of the TGF-β superfamily," Mechanisms of Development, 80:181-184 (1999).

Pashmforoush, M., et al., "Nkx2-5 Pathways and Congenital Heart Disease: Loss of Ventricular Myocyte Lineage Specification Leads to Progressive Cardiomyopathy and Complete Heart Block," Cell, 117:373-386 (2004).

Takao et al., "Identification of Rat Bone Morphogenetic Protein-3b (BMP-3b), a New Member of BMP-3", Biochemical and Biophysical Research Communications, 219(2)656-662(1996).

Teichmann, U., and Kessel, M., "Highly restricted BMP10 expression in the trabeculating myocardium of the chick embryo," Dev Genes Evol., 214:96-98 (2004).

Wang et al., "GDF-3 is an adipogenic cytokine under high fat dietary condition," *Biochemical and Biophysical Research Communications*, 321: 1024-1031 (2004).

Witthuhn et al., "Upregulation of Bone Morphogenetic Protein GDF-3/Vgr-2 Expression in Adipose Tissue of FABP4/aP2 Null Mice," *Cytokine*, 14: 129-135 (2001).

Chen, H., et al., "Overexpression of Bone Morphogenetic Protein 10 in Myocardium Disrupts Cardiac Postnatal Hypertrophic Growth," The Journal of Biological Chemistry, 281(37):27481-27491 (2006).

Beiboer et al., Guided selection of a Pan carcinoma specific antibody reveals similar binding characteristics yet structural divergence between the original murine antibody and its human equivalent. J. Mol. Bio.vol. 296 pp. 833-849 (2000).

Klimka et al., Human anti-CD30 recombinant antibodies by guided phange antibody selection using cell panning. British Journal of Cancer. vol. 83, pp. 252-260 (2000).

MacCallum et al., Antibody-antigen Interactions: Contact Analysis and Binding Site Topography. J. Mol. Biol. vol. 262 pp. 732-745 (1996).

Thies et al., "GDF-8 Propeptide Binds to GDF-8 and Antagonizes Biological Activity by Inhibiting GDF-8 Receptor Binding," Growth Factors, vol. 18, pp. 251-259 (2001).

* cited by examiner

Figure 1. Human GDF3 propeptide sequence (SEQ ID NO: 1) (226 aa).

QEYVFLQFLGLDKAPSPQKFQPVPYILKKIFQDREAAATTGVSRDLCYVKELGVRGNVL

RFLPDQGFFLYPKKISQASSCLQKLLYFNLSAIKEREQLTLAQLGLDLGPNSYYNLGPE

LELALFLVQEPHVWGQTTPKPGKMFVLRSVPWPQGAVHFNLLDVAKDWNDNPRKNFGLF

LEILVKEDRDSGVNFQPEDTCARLRCSLHASLLVVTLNPDQCHPSRKRR

Figure 2. Mouse GDF3 propeptide sequence (SEQ ID NO: 2) (230 aa).

SEFQDSDLLQFLGLEKAPSPHRFQPVPRVLRKIIRAREAAAASGASQDLCYVKELGVRG

NLLQLLPDQGFFLNTQKPFQDGSCLQKVLYFNLSAIKEKAKLTMAQLTLDLGPRSYYNL

RPELVVALSVVQDRGVWGRSHPKVGRLLFLRSVPGPQGQLQFNLQGALKDWSSNRLKNL

DLHLEILVKEDRYSRVTVQPENPCDPLLRSLHASLLVVTLNPKHCHPSSRKRR

Figure 3. Human GDF3 precursor sequence (SEQ ID NO: 3) (NP_065685, 364 aa).

MLRFLPDLAFSFLLILALGQAVQFQEYVFLQFLGLDKAPSPQKFQPVPYILKKIFQDRE
AAATTGVSRDLCYVKELGVRGNVLRFLPDQGFFLYPKKISQASSCLQKLLYFNLSAIKE
REQLTLAQLGLDLGPNSYYNLGPELELALFLVQEPHVWGQTTPKPGKMFVLRSVPWPQG
AVHFNLLDVAKDWNDNPRKNFGLFLEILVKEDRDSGVNFQPEDTCARLRCSLHASLLVV
TLNPDQCHPSRKRRAAIPVPKLSCKNLCHRHQLFINFRDLGWHKWIIAPKGFMANYCHG
ECPFSLTISLSSNYAFMQALMHAVDPEIPQAVCIPTKLSPISMLYQDNNDNVILRHYE
DMVVDECGCG

Figure 4. Mouse GDF3 precursor sequence (SEQ ID NO: 4) (NP_032134, 366 aa).

MQPYQRLLALGFLLLTLPWGQTSEFQDSDLLQFLGLEKAPSPHRFQPVPRVLRKIIRAR

EAAAASGASQDLCYVKELGVRGNLLQLLPDQGFFLNTQKPFQDGSCLQKVLYFNLSAIK

EKAKLTMAQLTLDLGPRSYYNLRPELVVALSVVQDRGVWGRSHPKVGRLLFLRSVPGPQ

GQLQFNLQGALKDWSSNRLKNLDLHLEILVKEDRYSRVTVQPENPCDPLLRSLHASLLV

VTLNPKHCHPSSRKRRAAISVPKGFCRNFCHRHQLFINFQDLGWHKWVIAPKGFMANYC

HGECPFSMTTYLSSNYAFMQALMHMADPKVPKAVCVPTKLSPISMLYQDSDKNVILRH

YEDMVVDECGCG

Figure 5. Nucleic acid sequence encoding a human GDF3 propeptide (SEQ ID NO: 5) (678 bp).

```
caagaatatgtctttctccaatttctgggcttagataaggcgccttcaccccagaagttccaacctgtgcc
ttatatcttgaagaaaattttccaggatcgcgaggcagcagcgaccactggggtctcccgagacttatgct
acgtaaaggagctgggcgtccgcgggaatgtacttcgctttctcccagaccaaggtttctttctttaccca
aagaaaatttcccaagcttcctcctgcctgcagaagctcctctactttaacctgtctgccatcaaagaaag
ggaacagttgacattggcccagctgggcctggacttggggcccaattcttactataacctgggaccagagc
tggaactggctctgttcctggttcaggagcctcatgtgtggggccagaccacccctaagccaggtaaaatg
tttgtgttgcggtcagtcccatggccacaaggtgctgttcacttcaacctgctggatgtagctaaggattg
gaatgacaaccccggaaaaatttcgggttattcctggagatactggtcaaagaagatagagactcagggg
tgaattttcagcctgaagacacctgtgccagactaagatgctcccttcatgcttccctgctggtggtgact
ctcaaccctgatcagtgccaccttctcggaaaaggaga
```

Figure 6. Nucleic acid sequence encoding a mouse GDF3 propeptide (SEQ ID NO: 6) (690 bp).

```
tccgagtttcaagactctgaccttttgcagtttctgggattagagaaagcgccttcacctcacaggttcca
acctgtgcctcgcgtcttaaggaaaatcatccgggctcgagaagccgctgcagccagtggggcctcgcagg
acttatgctacgtgaaggagctgggtgttcgtgggaacctgcttcagcttctcccagaccagggttttttc
cttaatacacagaaacctttccaagatggctcctgtctccagaaggtcctctattttaacttgtctgccat
caaagaaaaggcaaagttgaccatggcccagctgactctagacttggggcccaggtcctactataacctgc
gaccagagctggtggttgctctgtctgtggttcaggaccggggcgtgtggggcgatcccaccctaaggtg
ggcagattgcttttctgcggtctgtccctgggcctcaaggtcagctccagttcaacctgcagggtgcgct
taaggattggagcagcaaccgactgaagaatttggacttacacttagagattttggtcaaagaggacagat
actccagggtaactgtccagcccgagaacccctgtgacccgctgctccgctctctacatgcctcgctgctg
gtggtaaccctcaatcctaaacactgtcatccttcttccagaaaaaggagg
```

Figure 7. Nucleic acid sequence encoding a human GDF3 precursor protein (SEQ ID NO: 7) (nucleotides 37-1128 of NM_020634, 1092 bp).

```
atgcttcgtttcttgccagatttggctttcagcttcctgttaattctggctttgggccaggcagtccaatt
tcaagaatatgtctttctccaatttctgggcttagataaggcgccttcaccccagaagttccaacctgtgc
cttatatcttgaagaaaattttccaggatcgcgaggcagcagcgaccactggggtctcccgagacttatgc
tacgtaaaggagctgggcgtccgcgggaatgtacttcgctttctcccagaccaaggtttctttctttaccc
aaagaaaatttcccaagcttcctcctgcctgcagaagctcctctactttaacctgtctgccatcaaagaaa
gggaacagttgacattggcccagctgggcctggacttggggcccaattcttactataacctgggaccagag
ctggaactggctctgttcctggttcaggagcctcatgtgtggggccagaccacccctaagccaggtaaaat
gtttgtgttgcggtcagtcccatggccacaaggtgctgttcacttcaacctgctggatgtagctaaggatt
ggaatgacaaccccggaaaaatttcgggttattcctggagatactggtcaaagaagatagagactcaggg
gtgaattttcagcctgaagacacctgtgccagactaagatgctcccttcatgcttccctgctggtggtgac
tctcaaccctgatcagtgccaccttctcggaaaaggagagcagccatccctgtccccaagctttcttgta
agaacctctgccaccgtcaccagctattcattaacttccgggacctgggttggcacaagtggatcattgcc
cccaaggggttcatggcaaattactgccatggagagtgtcccttctcactgaccatctctctcaacagctc
caattatgctttcatgcaagccctgatgcatgccgttgacccagagatcccccaggctgtgtgtatcccca
ccaagctgtctcccatttccatgctctaccaggacaataatgacaatgtcattctacgacattatgaagac
atggtagtcgatgaatgtgggtgtggg
```

Figure 8. Nucleic acid sequence encoding a mouse GDF3 precursor protein (SEQ ID NO: 8) (nucleotides 122-1219 of NM_008108, 1098 bp).

```
atgcagccttatcaacggcttctggcgcttggcttccttctgttaaccctgccctggggccagacatccga
gtttcaagactctgacctttttgcagtttctgggattagagaaagcgccttcacctcacaggttccaacctg
tgcctcgcgtcttaaggaaaatcatccgggctcgagaagccgctgcagccagtggggcctcgcaggactta
tgctacgtgaaggagctgggtgttcgtgggaacctgcttcagcttctcccagaccagggttttttccttaa
tacacagaaacctttccaagatggctcctgtctccagaaggtcctctattttaacttgtctgccatcaaag
aaaaggcaaagttgaccatggcccagctgactctagacttggggcccaggtcctactataacctgcgacca
gagctggtggttgctctgtctgtggttcaggaccggggcgtgtggggcgatcccaccctaaggtgggcag
attgcttttctgcggtctgtccctgggcctcaaggtcagctccagttcaacctgcagggtgcgcttaagg
attggagcagcaaccgactgaagaatttggacttacacttagagattttggtcaaagaggacagatactcc
agggtaactgtccagcccgagaacccctgtgaccgctgctccgctctctacatgcctcgctgctggtggt
aaccctcaatcctaaacactgtcatccttcttccagaaaaaggagggcggccatctctgtccccaagggtt
tctgtaggaacttctgccaccgtcatcagctgttcatcaacttccaggacctggggttggcacaagtgggtc
atcgcccctaaggggttcatggcaaattactgtcatggagagtgcccttctcaatgaccacgtatttaaa
tagttccaattatgctttcatgcaggctctgatgcatatggctgaccccaaggtccccaaggctgtctgtg
tccccaccaagctctcgcccatctccatgctctatcaggatagtgataagaacgtcattctccgacattat
gaagacatggtagtcgatgagtgtgggtgtggg
```

Figure 9: Human GDF-3 Propeptide Binds to Mature Human GDF-3
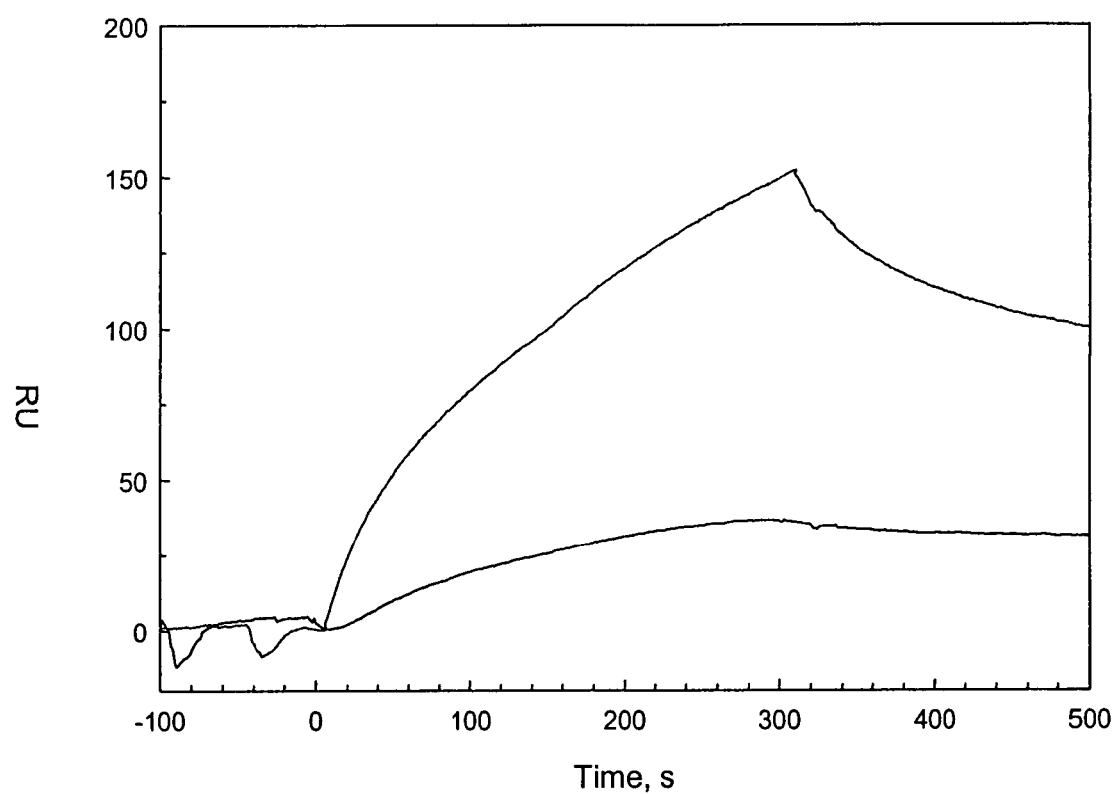

SEQUENCE LISTING

```
<160> NUMBER OF SEQ ID NOS: 10

<210> SEQ ID NO 1
<211> LENGTH: 226
<212> TYPE: PRT
<213> ORGANISM: Homo sapiens

<400> SEQUENCE: 1

Gln Glu Tyr Val Phe Leu Gln Phe Leu Gly Leu Asp Lys Ala Pro Ser
1               5                   10                  15

Pro Gln Lys Phe Gln Pro Val Pro Tyr Ile Leu Lys Lys Ile Phe Gln
            20                  25                  30

Asp Arg Glu Ala Ala Ala Thr Thr Gly Val Ser Arg Asp Leu Cys Tyr
        35                  40                  45

Val Lys Glu Leu Gly Val Arg Gly Asn Val Leu Arg Phe Leu Pro Asp
    50                  55                  60

Gln Gly Phe Phe Leu Tyr Pro Lys Lys Ile Ser Gln Ala Ser Ser Cys
65                  70                  75                  80

Leu Gln Lys Leu Leu Tyr Phe Asn Leu Ser Ala Ile Lys Glu Arg Glu
                85                  90                  95

Gln Leu Thr Leu Ala Gln Leu Gly Leu Asp Leu Gly Pro Asn Ser Tyr
            100                 105                 110

Tyr Asn Leu Gly Pro Glu Leu Glu Leu Ala Leu Phe Leu Val Gln Glu
        115                 120                 125

Pro His Val Trp Gly Gln Thr Thr Pro Lys Pro Gly Lys Met Phe Val
    130                 135                 140

Leu Arg Ser Val Pro Trp Pro Gln Gly Ala Val His Phe Asn Leu Leu
145                 150                 155                 160

Asp Val Ala Lys Asp Trp Asn Asp Asn Pro Arg Lys Asn Phe Gly Leu
```

```
                165                 170                 175
Phe Leu Glu Ile Leu Val Lys Glu Asp Arg Asp Ser Gly Val Asn Phe
            180                 185                 190
Gln Pro Glu Asp Thr Cys Ala Arg Leu Arg Cys Ser Leu His Ala Ser
        195                 200                 205
Leu Leu Val Val Thr Leu Asn Pro Asp Gln Cys His Pro Ser Arg Lys
    210                 215                 220
Arg Arg
225

<210> SEQ ID NO 2
<211> LENGTH: 230
<212> TYPE: PRT
<213> ORGANISM: Mus musculus

<400> SEQUENCE: 2

Ser Glu Phe Gln Asp Ser Asp Leu Leu Gln Phe Leu Gly Leu Glu Lys
1               5                   10                  15
Ala Pro Ser Pro His Arg Phe Gln Pro Val Pro Arg Val Leu Arg Lys
            20                  25                  30
Ile Ile Arg Ala Arg Glu Ala Ala Ala Ser Gly Ala Ser Gln Asp
        35                  40                  45
Leu Cys Tyr Val Lys Glu Leu Gly Val Arg Gly Asn Leu Leu Gln Leu
    50                  55                  60
Leu Pro Asp Gln Gly Phe Phe Leu Asn Thr Gln Lys Pro Phe Gln Asp
65                  70                  75                  80
Gly Ser Cys Leu Gln Lys Val Leu Tyr Phe Asn Leu Ser Ala Ile Lys
                85                  90                  95
Glu Lys Ala Lys Leu Thr Met Ala Gln Leu Thr Leu Asp Leu Gly Pro
            100                 105                 110
Arg Ser Tyr Tyr Asn Leu Arg Pro Glu Leu Val Val Ala Leu Ser Val
        115                 120                 125
Val Gln Asp Arg Gly Val Trp Gly Arg Ser His Pro Lys Val Gly Arg
    130                 135                 140
Leu Leu Phe Leu Arg Ser Val Pro Gly Pro Gln Gly Gln Leu Gln Phe
145                 150                 155                 160
Asn Leu Gln Gly Ala Leu Lys Asp Trp Ser Ser Asn Arg Leu Lys Asn
                165                 170                 175
Leu Asp Leu His Leu Glu Ile Leu Val Lys Glu Asp Arg Tyr Ser Arg
            180                 185                 190
Val Thr Val Gln Pro Glu Asn Pro Cys Asp Pro Leu Leu Arg Ser Leu
        195                 200                 205
His Ala Ser Leu Leu Val Val Thr Leu Asn Pro Lys His Cys His Pro
    210                 215                 220
Ser Ser Arg Lys Arg Arg
225                 230

<210> SEQ ID NO 3
<211> LENGTH: 364
<212> TYPE: PRT
<213> ORGANISM: Homo sapiens

<400> SEQUENCE: 3

Met Leu Arg Phe Leu Pro Asp Leu Ala Phe Ser Phe Leu Leu Ile Leu
1               5                   10                  15
Ala Leu Gly Gln Ala Val Gln Phe Gln Glu Tyr Val Phe Leu Gln Phe
            20                  25                  30
```

```
Leu Gly Leu Asp Lys Ala Pro Ser Pro Gln Lys Phe Gln Pro Val Pro
            35                  40                  45

Tyr Ile Leu Lys Lys Ile Phe Gln Asp Arg Glu Ala Ala Thr Thr
 50                  55                  60

Gly Val Ser Arg Asp Leu Cys Tyr Val Lys Glu Leu Gly Val Arg Gly
 65                  70                  75                  80

Asn Val Leu Arg Phe Leu Pro Asp Gln Gly Phe Phe Leu Tyr Pro Lys
                85                  90                  95

Lys Ile Ser Gln Ala Ser Ser Cys Leu Gln Lys Leu Leu Tyr Phe Asn
                100                 105                 110

Leu Ser Ala Ile Lys Glu Arg Glu Gln Leu Thr Leu Ala Gln Leu Gly
                115                 120                 125

Leu Asp Leu Gly Pro Asn Ser Tyr Tyr Asn Leu Gly Pro Glu Leu Glu
            130                 135                 140

Leu Ala Leu Phe Leu Val Gln Glu Pro His Val Trp Gly Gln Thr Thr
145                 150                 155                 160

Pro Lys Pro Gly Lys Met Phe Val Leu Arg Ser Val Pro Trp Pro Gln
                165                 170                 175

Gly Ala Val His Phe Asn Leu Leu Asp Val Ala Lys Asp Trp Asn Asp
                180                 185                 190

Asn Pro Arg Lys Asn Phe Gly Leu Phe Leu Glu Ile Leu Val Lys Glu
                195                 200                 205

Asp Arg Asp Ser Gly Val Asn Phe Gln Pro Glu Asp Thr Cys Ala Arg
            210                 215                 220

Leu Arg Cys Ser Leu His Ala Ser Leu Leu Val Val Thr Leu Asn Pro
225                 230                 235                 240

Asp Gln Cys His Pro Ser Arg Lys Arg Arg Ala Ala Ile Pro Val Pro
                245                 250                 255

Lys Leu Ser Cys Lys Asn Leu Cys His Arg His Gln Leu Phe Ile Asn
                260                 265                 270

Phe Arg Asp Leu Gly Trp His Lys Trp Ile Ile Ala Pro Lys Gly Phe
            275                 280                 285

Met Ala Asn Tyr Cys His Gly Glu Cys Pro Phe Ser Leu Thr Ile Ser
            290                 295                 300

Leu Asn Ser Ser Asn Tyr Ala Phe Met Gln Ala Leu Met His Ala Val
305                 310                 315                 320

Asp Pro Glu Ile Pro Gln Ala Val Cys Ile Pro Thr Lys Leu Ser Pro
                325                 330                 335

Ile Ser Met Leu Tyr Gln Asp Asn Asn Asp Asn Val Ile Leu Arg His
                340                 345                 350

Tyr Glu Asp Met Val Val Asp Glu Cys Gly Cys Gly
                355                 360
```

<210> SEQ ID NO 4
<211> LENGTH: 366
<212> TYPE: PRT
<213> ORGANISM: Mus musculus

<400> SEQUENCE: 4

```
Met Gln Pro Tyr Gln Arg Leu Leu Ala Leu Gly Phe Leu Leu Leu Thr
 1               5                  10                  15

Leu Pro Trp Gly Gln Thr Ser Glu Phe Gln Asp Ser Asp Leu Leu Gln
                20                  25                  30

Phe Leu Gly Leu Glu Lys Ala Pro Ser Pro His Arg Phe Gln Pro Val
            35                  40                  45
```

```
Pro Arg Val Leu Arg Lys Ile Ile Arg Ala Arg Glu Ala Ala Ala
    50                  55                  60
Ser Gly Ala Ser Gln Asp Leu Cys Tyr Val Lys Glu Leu Gly Val Arg
65                  70                  75                  80
Gly Asn Leu Leu Gln Leu Leu Pro Asp Gln Gly Phe Phe Leu Asn Thr
                85                  90                  95
Gln Lys Pro Phe Gln Asp Gly Ser Cys Leu Gln Lys Val Leu Tyr Phe
            100                 105                 110
Asn Leu Ser Ala Ile Lys Glu Lys Ala Lys Leu Thr Met Ala Gln Leu
        115                 120                 125
Thr Leu Asp Leu Gly Pro Arg Ser Tyr Tyr Asn Leu Arg Pro Glu Leu
    130                 135                 140
Val Val Ala Leu Ser Val Val Gln Asp Arg Gly Val Trp Gly Arg Ser
145                 150                 155                 160
His Pro Lys Val Gly Arg Leu Leu Phe Leu Arg Ser Val Pro Gly Pro
                165                 170                 175
Gln Gly Gln Leu Gln Phe Asn Leu Gln Gly Ala Leu Lys Asp Trp Ser
            180                 185                 190
Ser Asn Arg Leu Lys Asn Leu Asp Leu His Leu Glu Ile Leu Val Lys
        195                 200                 205
Glu Asp Arg Tyr Ser Arg Val Thr Val Gln Pro Glu Asn Pro Cys Asp
    210                 215                 220
Pro Leu Leu Arg Ser Leu His Ala Ser Leu Leu Val Thr Leu Asn
225                 230                 235                 240
Pro Lys His Cys His Pro Ser Ser Arg Lys Arg Ala Ala Ile Ser
                245                 250                 255
Val Pro Lys Gly Phe Cys Arg Asn Phe Cys His Arg His Gln Leu Phe
            260                 265                 270
Ile Asn Phe Gln Asp Leu Gly Trp His Lys Trp Val Ile Ala Pro Lys
        275                 280                 285
Gly Phe Met Ala Asn Tyr Cys His Gly Glu Cys Pro Phe Ser Met Thr
    290                 295                 300
Thr Tyr Leu Asn Ser Ser Asn Tyr Ala Phe Met Gln Ala Leu Met His
305                 310                 315                 320
Met Ala Asp Pro Lys Val Pro Lys Ala Val Cys Val Pro Thr Lys Leu
                325                 330                 335
Ser Pro Ile Ser Met Leu Tyr Gln Asp Ser Asp Lys Asn Val Ile Leu
            340                 345                 350
Arg His Tyr Glu Asp Met Val Val Asp Glu Cys Gly Cys Gly
        355                 360                 365

<210> SEQ ID NO 5
<211> LENGTH: 678
<212> TYPE: DNA
<213> ORGANISM: Homo sapiens

<400> SEQUENCE: 5
caagaatatg tctttctcca atttctgggc ttagataagg cgccttcacc ccagaagttc      60
caacctgtgc cttatatctt gaagaaaatt ttccaggatc gcgaggcagc agcgaccact     120
ggggtctccc gagacttatg ctacgtaaag gagctgggcg tccgcgggaa tgtacttcgc     180
tttctcccag accaaggttt ctttctttac ccaagaaaaa ttcccaagc ttcctcctgc      240 ctgcagaagc tcctctactt taacctgtct gccatcaaag aaagggaaca gttgacattg     300
gcccagctgg gcctggactt ggggcccaat tcttactata acctgggacc agagctggaa     360
```

```
ctggctctgt tcctggttca ggagcctcat gtgtggggcc agaccacccc taagccaggt    420
aaaatgtttg tgttgcggtc agtcccatgg ccacaaggtg ctgttcactt caacctgctg    480
gatgtagcta aggattggaa tgacaacccc cggaaaaatt tcgggttatt cctggagata    540
ctggtcaaag aagatagaga ctcaggggtg aatttcagc ctgaagacac ctgtgccaga     600
ctaagatgct cccttcatgc ttccctgctg gtggtgactc tcaaccctga tcagtgccac    660
ccttctcgga aaggaga                                                   678
```

```
<210> SEQ ID NO 6
<211> LENGTH: 690
<212> TYPE: DNA
<213> ORGANISM: Mus musculus

<400> SEQUENCE: 6
tccgagtttc aagactctga ccttttgcag tttctgggat tagagaaagc gccttcacct    60
cacaggttcc aacctgtgcc tcgcgtctta aggaaaatca tccgggctcg agaagccgct   120
gcagccagtg gggcctcgca ggacttatgc tacgtgaagg agctgggtgt tcgtgggaac   180
ctgcttcagc ttctcccaga ccagggtttt ttccttaata cacagaaacc tttccaagat   240
ggctcctgtc tccagaaggt cctctatttt aacttgtctg ccatcaaaga aaggcaaag    300 ttgaccatgg cccagctgac tctagacttg gggcccaggt cctactataa cctgcgacca   360
gagctggtgg ttgctctgtc tgtggttcag gaccggggcg tgtggggcg atcccaccct    420 aaggtgggca gattgctttt tctgcggtct gtccctgggc tcaaggtca gctccagttc     480 aacctgcagg gtgcgcttaa ggattggagc agcaaccgac tgaagaattt ggacttacac   540
ttagagattt tggtcaaaga ggacagatac tccagggtaa ctgtccagcc cgagaacccc   600
tgtgacccgc tgctccgctc tctacatgcc tcgctgctgg tggtaaccct caatcctaaa   660
cactgtcatc cttcttccag aaaaaggagg                                     690
```

```
<210> SEQ ID NO 7
<211> LENGTH: 1092
<212> TYPE: DNA
<213> ORGANISM: Homo sapiens

<400> SEQUENCE: 7
atgcttcgtt tcttgccaga tttggctttc agcttcctgt taattctggc tttgggccag    60
gcagtccaat tcaagaata tgtctttctc caatttctgg cttagataa ggcgccttca     120 ccccagaagt tccaacctgt gccttatatc ttgaagaaaa ttttccagga tcgcgaggca   180
gcagcgacca ctggggtctc ccagacttta tgctacgtaa aggagctggg cgtccgcggg   240
aatgtacttc gctttctccc agaccaaggt ttctttcttt acccaaagaa aatttcccaa   300
gcttcctcct gcctgcagaa gctcctctac tttaacctgt ctgccatcaa agaaagggaa   360
cagttgacat ggcccagct gggcctggac ttggggccca attcttacta taacctggga   420
ccagagctgg aactggctct gttcctggtt caggagcctc atgtgtgggg ccagaccacc   480
cctaagccag gtaaaatgtt tgtgttgcgg tcagtcccat ggccacaagg tgctgttcac   540
ttcaacctgc tggatgtagc taaggattgg aatgacaacc ccggaaaaa tttcgggtta   600 ttcctggaga tactggtcaa agaagataga gactcagggg tgaattttca gcctgaagac   660
acctgtgcca gactaagatg ctcccttcat gcttccctgc tggtggtgac tctcaaccct   720
gatcagtgcc acccttctcg gaaaaggaga gcagccatcc ctgtcccaa gctttcttgt   780 aagaacctct gccaccgtca ccagctattc attaacttcc gggacctggg ttggcacaag   840
```

```
tggatcattg cccccaaggg gttcatggca aattactgcc atggagagtg tcccttctca        900
ctgaccatct ctctcaacag ctccaattat gctttcatgc aagccctgat gcatgccgtt        960
gacccagaga tcccccaggc tgtgtgtatc cccaccaagc tgtctcccat ttccatgctc       1020
taccaggaca ataatgacaa tgtcattcta cgacattatg aagacatggt agtcgatgaa       1080
tgtgggtgtg gg                                                            1092

<210> SEQ ID NO 8
<211> LENGTH: 1098
<212> TYPE: DNA
<213> ORGANISM: Mus musculus

<400> SEQUENCE: 8
atgcagcctt atcaacggct tctggcgctt ggcttccttc tgttaaccct gccctggggc         60
cagacatccg agtttcaaga ctctgacctt ttgcagtttc tgggattaga gaaagcgcct        120
tcacctcaca ggttccaacc tgtgcctcgc gtcttaagga aaatcatccg ggctcgagaa        180
gccgctgcag ccagtggggc ctcgcaggac ttatgctacg tgaaggagct gggtgttcgt        240
gggaacctgc ttcagcttct cccagaccag ggttttttcc ttaatacaca gaaacctttc        300
caagatggct cctgtctcca gaaggtcctc tattttaact tgtctgccat caaagaaaag        360
gcaaagttga ccatggccca gctgactcta gacttgggc ccaggtccta ctataacctg        420
cgaccagagc tggtggttgc tctgtctgtg gttcaggacc ggggcgtgtg ggggcgatcc        480
caccctaagg tgggcagatt gcttttctg cggtctgtcc ctgggcctca aggtcagctc        540
cagttcaacc tgcagggtgc gcttaaggat tggagcagca accgactgaa gaatttggac        600
ttacacttag agattttggt caaagaggac agatactcca gggtaactgt ccagcccgag        660 aaccctgtg accgctgct ccgctctcta catgcctcgc tgctggtggt aaccctcaat        720
cctaaacact gtcatccttc ttccagaaaa aggagggcgg ccatctctgt ccccaagggt        780
ttctgtagga acttctgcca ccgtcatcag ctgttcatca acttccagga cctgggttgg        840
cacaagtggg tcatcgcccc taaggggttc atggcaaatt actgtcatgg agagtgcccc        900
ttctcaatga ccacgtattt aaatagttcc aattatgctt tcatgcaggc tctgatgcat        960
atggctgacc ccaaggtccc caaggctgtc tgtgtcccca ccaagctctc gcccatctcc       1020
atgctctatc aggatagtga taagaacgtc attctccgac attatgaaga catggtagtc       1080
gatgagtgtg ggtgtggg                                                     1098

<210> SEQ ID NO 9
<211> LENGTH: 75
<212> TYPE: PRT
<213> ORGANISM: Homo sapiens

<400> SEQUENCE: 9

Leu Lys Cys Val Cys Leu Leu Cys Asp Ser Ser Asn Phe Thr Cys Gln
1               5                   10                  15

Thr Glu Gly Ala Cys Trp Ala Ser Val Met Leu Thr Asn Gly Lys Glu
            20                  25                  30

Gln Val Ile Lys Ser Cys Val Ser Leu Pro Glu Leu Asn Ala Gln Val
        35                  40                  45

Phe Cys His Ser Ser Asn Asn Val Thr Lys Thr Glu Cys Cys Phe Thr
    50                  55                  60

Asp Phe Cys Asn Asn Ile Thr Leu His Leu Pro
65                  70                  75
```

```
<210> SEQ ID NO 10
<211> LENGTH: 70
<212> TYPE: PRT
<213> ORGANISM: Homo sapiens

<400> SEQUENCE: 10

Ala Leu Leu Cys Ala Cys Thr Ser Cys Leu Gln Ala Asn Tyr Thr Cys
1               5                   10                  15

Glu Thr Asp Gly Ala Cys Met Val Ser Ile Phe Asn Leu Asp Gly Met
            20                  25                  30

Glu His His Val Arg Thr Cys Ile Pro Lys Val Glu Leu Val Pro Ala
        35                  40                  45

Gly Lys Pro Phe Tyr Cys Leu Ser Ser Glu Asp Leu Arg Asn Thr His
    50                  55                  60

Cys Cys Tyr Thr Asp Tyr
65              70
```

US 8,293,238 B2

GDF3 ANTIBODIES AND RELATED METHODS

RELATED APPLICATIONS

This application is a continuation of U.S. Ser. No. 11/165,963, filed on Jun. 24, 2005, which claims the benefit of U.S. Provisional Application No. 60/583,073, filed Jun. 24, 2004, which applications are hereby incorporated by reference in their entireties.

SEQUENCE LISTING

The instant application contains a Sequence Listing, which has been submitted via EFS-Web and is hereby incorporated by reference in its entirety. Said ASCII copy, created on Sep. 2, 2011 is named PHPHP02008substitute_seq_txt and is 17,132 bytes in size.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Many of members of the superfamily perform important functions during embryonic development in pattern formation and tissue specification and can influence a variety of differentiation processes, including adipogenesis, myogenesis, chondrogenesis, cardiogenesis, hematopoiesis, and epithelial cell differentiation. The family is divided into two general branches: the BMP/GDF and the TGF-beta/Activin/BMP10 branches, whose members have diverse, often complementary effects. By manipulating the activity of a member of the TGF-beta family, it is often possible to cause significant physiological changes in an organism. For example, the Piedmontese and Belgian Blue cattle breeds carry a loss-of-function mutation in the GDF-8/myostatin gene that causes a marked increase in muscle mass. Grobet et al., Nat Genet. 1997 September; 17(1):71-4. Changes in fat, bone, cartilage, muscle and other tissues may be achieved by agonizing or antagonizing signaling that is mediated by an appropriate TGF-beta family member. Thus, there is a need for agents (e.g., polypeptides) that function as potent regulators of TGF-beta signaling.

SUMMARY OF THE INVENTION

In certain aspects, the present disclosure provides GDF3 propeptides. Such propeptides may be used for the treatment of a variety of disorders, particularly disorders relating to body fat content or body weight, such as obesity and Type II diabetes. GDF3 propeptides may also be used to antagonize GDF3 generally, in any GDF3 related process, including, for example, cancers associated with GDF3 activity. GDF3 propeptides may antagonize other members of the BMP family and may therefore be useful in the treatment of additional disorders. Examples of GDF3 propeptides include the naturally occurring propeptides of GDF3, as well as functional variants thereof. Additionally, the disclosure provides antibodies that bind a mature GDF3 peptide in a manner similar to a GDF3 propeptide. Such antibodies may also be used to treat disorders relating to body fat content or body weight or other GDF3 related disorders.

In certain aspects, the disclosure provides pharmaceutical preparations comprising a GDF3 propeptide that binds to a mature GDF3 polypeptide, and a pharmaceutically acceptable carrier. Optionally the GDF3 propeptide binds to a mature GDF3 with a Kd less than 10 micromolar or less than 1 micromolar, 100, 10 or 1 nanomolar. Optionally, the GDF3 propeptide inhibits an activity of mature GDF3, such as receptor binding or intracellular signal transduction events triggered by GDF3. A GDF3 propeptide for use in such a preparation may be any of those disclosed herein, such as a polypeptide having an amino acid sequence of SEQ ID NO: 1 or 2 or having an amino acid sequence that is at least 80%, 85%, 90%, 95%, 97% or 99% identical to an amino acid sequence of SEQ ID NO: 1 or 2. A GDF3 propeptide may include a functional fragment of a natural GDF3 propeptide, such as one comprising at least 10, 20 or 30 amino acids of SEQ ID NO:1 or 2. A GDF3 propeptide will generally not contain a full-length or functional portion of a mature GDF3 polypeptide, and preferably a GDF3 propeptide will include no more than 50, 40, 30, 20, 10 or 5 amino acids of a mature portion of a GDF3 polypeptide. A GDF3 propeptide may include one or more alterations in the amino acid sequence relative to a naturally occurring GDF3 propeptide. The alteration in the amino acid sequence may, for example, alter glycosylation of the polypeptide when produced in a mammalian, insect or other eukaryotic cell or alter proteolytic cleavage of the polypeptide relative to the naturally occurring GDF3 polypeptide. A GDF3 propeptide may be a fusion protein that has, as one domain, a GDF3 propeptide and one or more additional domains that provide a desirable property, such as improved pharmacokinetics, easier purification, targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. A GDF3 propeptide fusion protein may include an immunoglobulin Fc domain or a serum albumin domain. A fusion protein may include a purification subsequence, such as an epitope tag, a FLAG tag, a polyhistidine sequence, and a GST fusion. A GDF3 propeptide may be fused to a polypeptide that blocks binding to a type I receptor. Optionally, a GDF3 propeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. A pharmaceutical preparation may also include one or more additional compounds such as a compound that is used to treat a GDF3 associated disorder. Preferably, a pharmaceutical preparation is substantially pyrogen free. Preferably, a pharmaceutical composition comprising a GDF3 propeptide will not include, as a separate component, an active mature GDF3 protein.

In certain aspects, the disclosure provides nucleic acids encoding a GDF3 propeptide that do not encode a complete, translatable mature portion of a GDF3. An isolated polynucleotide may comprise a coding sequence for a GDF3 propeptide, such as described above. An isolated nucleic acid may include a sequence coding for a GDF3 propeptide and a sequence that would code for part or all of a mature portion, but for a stop codon positioned within the mature portion or positioned between the propeptide and the mature portion. For example, an isolated polynucleotide may comprise a full-length GDF3 polynucleotide sequence such as SEQ ID NO:7 or 8, or a partially truncated version, said isolated polynucleotide further comprising a transcription termination codon at least three hundred nucleotides before the 3'-terminus or otherwise positioned such that translation of the polynucleotide gives rise to a GDF3 propeptide optionally fused to a truncated mature peptide portion. Nucleic acids disclosed herein may be operably linked to a promoter for expression, and the disclosure provides cells transformed with such recombinant polynucleotides. Preferably the cell is a mammalian cell such as a CHO cell.

In certain aspects, the disclosure provides methods for making a GDF3 propeptide. Such a method may include expressing any of the propeptide encoding nucleic acids disclosed herein in a suitable cell, such as a Chinese hamster ovary (CHO) cell. Such a method may comprise: a) culturing a cell under conditions suitable for expression of the propeptide, wherein said cell is transformed with a GDF3 propeptide expression construct; and b) recovering the propeptide so expressed. Propeptides may be recovered as crude, partially purified or highly purified fractions using any of the well known techniques for obtaining protein from cell cultures.

In certain aspects, the disclosure provides methods for inhibiting adipocyte growth or proliferation, in vivo or ex vivo. A method for inhibiting adipocyte growth or proliferation may comprise contacting an adipocyte with an effective amount of a GDF3 propeptide disclosed herein. Optionally, the adipocyte is a mammalian adipocyte, such as a human adipocyte. Similarly, a GDF3 propeptide may be used to inhibit the growth, proliferation or differentiation of an adipocyte precursor cell.

In certain aspects, a GDF3 polypeptide disclosed herein may be used in a method for treating a subject having a disorder associated with abnormal cell growth and differentiation. A method may comprise administering to a subject in need thereof an effective amount of a GDF3 propeptide.

In certain aspects, the disclosure provides methods for antagonizing a GDF3 activity in a mammal or in a cell, ex vivo or in vivo. A method may comprise administering to the mammal or contacting the cell with a GDF3 propeptide. The effect of a GDF3 propeptide on GDF3 signaling may be monitored by detecting a signal transduction event mediated by mature GDF3. The effect of a GDF3 propeptide on mature GDF3 activity may also be monitored by detecting the degree of cell proliferation of GDF3-sensitive cell type. Optionally, a cell to be contacted is a mammalian cell, such as a human cell, and preferably an adipocyte or an adipocyte precursor cell.

In certain aspects, the disclosure provides a use of a GDF3 propeptide for making a medicament for the treatment of a disorder associated with unwanted fat content or body weight or other GDF3 associated disorders.

In further aspects, the disclosure provides methods for identifying an agent that may be used for treating a GDF3 associated disorder. A method may comprise: a) identifying a test agent that binds a mature GDF3 polypeptide competitively with a GDF3 propeptide; and b) evaluating the effect of the agent on a heart disorder. A test agent may be, for example, a variant GDF3 propeptide, an antibody, or a small molecule. In further aspects, the disclosure provides methods for identifying an agent that modulates adipocyte proliferation or growth. A method may comprise (a) identifying a test agent that binds a mature portion of GDF3 competitively with a GDF3 propeptide; and (b) evaluating the effect of the agent on adipocyte proliferation or growth. Similar methods may be used with adipocyte precursor cells.

BRIEF DESCRIPTION OF THE DRAWINGS

FIG. 1 shows a human GDF3 propeptide amino acid sequence (SEQ ID NO: 1). One, or all three, of the underlined cysteine residues may be altered to a non-cysteine amino acid to improve protein expression. Any of the residues in the C-terminal sequence HPSRKRR may also be removed during protein processing.

FIG. 2 shows a mouse GDF3 propeptide amino acid sequence (SEQ ID NO: 2).

FIG. 3 shows a human GDF3 precursor amino acid sequence (SEQ ID NO: 3). The signal peptide (residues 1-24) is underlined; the prodomain (residues 25-250) is in bold, also referred to as SEQ ID NO: 1; and the mature protein (residues 251-364) is shaded. The potential N-linked glycosylation sites are boxed.

FIG. 4 shows a mouse GDF3 precursor amino acid sequence (SEQ ID NO: 4). The signal peptide (residues 1-22) is underlined; the prodomain (residues 23-252) is in bold, also referred to as SEQ ID NO: 2; and the mature protein (residues 253-366) is shaded. The potential N-linked glycosylation sites are boxed.

FIG. 5 shows a nucleic acid sequence encoding a human GDF3 propeptide (SEQ ID NO: 5).

FIG. 6 shows a nucleic acid sequence encoding a mouse GDF3 propeptide (SEQ ID NO: 6).

FIG. 7 shows a nucleic acid sequence encoding a human GDF3 precursor protein (SEQ ID NO: 7).

FIG. 8 shows a nucleic acid sequence encoding a mouse GDF3 precursor protein (SEQ ID NO: 8).

FIG. 9 shows binding of a GDF3 Propeptide-Fc fusion to mature GDF3 protein. GDF3 propeptide was immobilized on a Biacore™ chip. Conditioned media obtained from cells expressing mature GDF3 was injected onto the chip at 50 µl/min. The upper trace shows the binding of GDF3 to the propeptide. The lower trace shows the absence of binding in a control reaction where media from cells not expressing GDF3 was injected onto the chip.

DETAILED DESCRIPTION OF THE INVENTION

1. Overview

In certain aspects, the present invention relates to GDF3 propeptides. As used herein, the term "GDF3" refers to a family of GDF3 proteins and GDF3-related proteins, derived from any species, as well as variants thereof. Members of the GDF3 family are generally encoded as a larger precursor, and members of the family share a region of high homology near the C-terminus, corresponding generally to the mature portion. For example, a human GDF3 mature polypeptide shares about 65% amino acid identity with a mouse GDF3 mature polypeptide. A naturally occurring GDF3 protein is generally encoded as a larger precursor that typically contains a signal sequence at its N-terminus followed by a cleavage site and a propeptide, followed by another dibasic amino acid cleavage site and a mature domain. A propeptide is generally the portion that is N-terminal to the mature domain and C-terminal to the signal peptide or any portion thereof that retains functional activity. Optionally, a GDF3 propeptide, after cleavage, reassociates with its mature peptide covalently or non-covalently, as in the case of insulin, relaxin, inhibin, activin, and TGF-β. The term "GDF3 propeptide" is used to refer to polypeptides comprising any naturally occurring propeptide of a GDF3 family member as well as any variants thereof (including mutants, fragments and peptidomimetic forms) that retain a useful activity. As used herein, GDF3 propeptides include fragments, functional variants, and modified forms (e.g., peptidomimetic forms) of GDF3 propeptides. A "GDF3 propeptide" will not include a full-length mature GDF3 domain, although a GDF3 propeptide may include portions of the mature domain, particularly portions that are not fully functional. For example, a GDF3 propeptide may contain fewer than 50, 40, 30, 20, 10 or 5 amino acids of its cognate mature domain.

Examples of GDF3 precursor proteins include human GDF3 and mouse GDF3 (also called Vgr-2). These precursor sequences are illustrated in FIGS. 3 and 4, respectively, and include signal peptide, propeptide, and mature peptide.

GDF-3 transcripts were detected primarily in adult bone marrow, spleen, thymus, and adipose tissue (McPherron et al., 1993, J Biol Chem. 268:3444-9). Expression of human GDF3 was also found in human embryonal carcinoma (EC) cell lines and in primary testicular germ cell tumors (TGCTs) of adolescents and adults. Thus human GDF3 represents an embryonal carcinoma stem cell-associated marker both in vitro and in vivo (Caricasole et al., 1998, Oncogene 16:95-103). Further, expression of mouse GDF3 homolog gene (also called Vgr2) was found at highest levels during midgestation mouse development, and its transcripts were localized to the osteogenic zone of developing bone (Jones et al, 1996, Mol Endocrinol. 6:1961-8). Recently, a linkage between GDF3 expression and adipocyte fatty acid metabolism was found (Witthuhn et al., 2001, Cytokine 14:129-135). In addition, it was recently found that human GDF3 gene is expressed in pluripotent cells and mapped to chromosome 12p13, a hotspot for teratocarcinoma (Clark, et al., 2004, Stem Cells 22(2):169-79). Accordingly, a GDF3 peptide (including a GDF3 mature propeptide and a GDF3 propeptide) disclosed herein may be used to treat a variety of disorders, including obesity, tumors, osteoporosis or other disorders related to undesirable GDF3 activity.

In September 2004, Wang et al. (Biochem Biophys Res Commun. 2004 Sep. 3; 321(4):1024-31) published data confirming the role of GDF-3 in regulating body weight and body fat content. Wang et al. found that overexpression of GDF-3 in mice caused weight gain when the mice were fed a high fat diet. The mice exhibited greatly increased adipose tissue mass, increased body adiposity, highly hypertrophic adipocytes, hepatic steatosis, and elevated plasma leptin. GDF-3 stimulated peroxisome proliferator activated receptor (PPAR) expression in adipocytes. PPAR is a nuclear receptor that regulates adipogenesis.

Thus, a preferred use of GDF-3 propeptides disclosed herein is for the purpose of treating obesity in subjects in need thereof.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants/sequence variants Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Λ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. GDF3 Propeptides

In certain aspects, the invention relates to GDF3 propeptides, including fragments, functional variants, and modified forms. Preferably any such variations will have biological activities that are similar to or the same as biological activities of their corresponding wild-type GDF3 propeptides. For example, a GDF3 propeptide of the invention may bind to and inhibit a function of a GDF3 mature protein. Optionally, a GDF3 propeptide regulates growth of a tissue such as fat, bone, cartilage, and muscle. In a specific embodiment, a GDF3 propeptide influences the amount of adipose tissue in a subject. Examples of GDF3 propeptides include a human GDF3 propeptide (SEQ ID NO: 1) and a mouse GDF3 propeptide (SEQ ID NO: 2).

In one specific example, human GDF3 cDNA (SEQ ID NO: 7, FIG. 7) encodes a 364-amino acid precursor protein (SEQ ID NO: 3, FIG. 3). Cleavage of the human GDF3 precursor protein at a putative polybasic proteolytic cleavage site generates a mature GDF3 protein consisting of 114 amino acids (FIG. 3) and a GDF3 propeptide consisting of 226 amino acids (FIGS. 1 and 3; SEQ ID NO: 1). The human GDF3 propeptide contains potential glycosylation sites (FIG. 3).

In another specific example, mouse GDF3 cDNA (SEQ ID NO: 8, FIG. 8) encodes a 366-amino acid precursor protein. Cleavage of the mouse GDF3 precursor protein at a putative polybasic proteolytic cleavage site generates a mouse mature GDF3 protein consisting of 114 amino acids and a GDF3 propeptide consisting of 230 amino acids (FIGS. 2 and 4; SEQ ID NO: 2). The mouse GDF3 propeptide contains a potential glycosylation site (FIG. 4).

In certain embodiments, isolated fragments of the GDF3 propeptides can be obtained by screening polypeptides recombinantly produced from the corresponding fragment of the nucleic acid encoding a GDF3 propeptide (e.g., SEQ ID NO: 1 or 2). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function, for example, as antagonists (inhibitors) or agonists (activators) of GDF3 activity.

In certain embodiments, a functional variant of the GDF3 propeptides has an amino acid sequence that is at least 75% identical to an amino acid sequence as set forth in SEQ ID NO: 1 or 2. In certain cases, the functional variant has an amino acid sequence at least 80%, 85%, 90%, 95%, 97%, 98%, 99% or 100% identical to an amino acid sequence as set forth in SEQ ID NO: 1 or 2.

In certain embodiments, the present invention contemplates making functional variants by modifying the structure of a GDF3 propeptide for such purposes as enhancing therapeutic efficacy, or stability (e.g., ex vivo shelf life and resistance to proteolytic degradation in vivo). Such modified GDF3 propeptides when designed to retain at least one activity of the naturally-occurring form of the GDF3 propeptides, are considered functional equivalents of the naturally-occurring propeptides. Modified GDF3 propeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a GDF3 propeptide results in a functional homolog can be readily determined by assessing the ability of the variant propeptide to produce a response in cells in a fashion similar to the wild-type propeptide.

In certain embodiments, the present invention contemplates making mutations in the RXXR proteolytic cleavage site of the GDF3 sequence to make the site less susceptible to proteolytic cleavage. Computer analysis (using a commercially available software, e.g., MacVector, Omega, PCGene, Molecular Simulation, Inc.) can be used to identify proteolytic cleavage sites. As will be recognized by one of skill in the art, most of the described mutations, variants or modifications may be made at the nucleic acid level or, in some cases, by post translational modification or chemical synthesis. Such techniques are well known in the art. For example, the cleavage site may be modified to include one or more glycosylation sites that block cleavage. Inhibition of cleavage will give rise to a covalently linked (i.e., uncleaved) GDF3 propeptide-mature domain fusion. Such an uncleaved GDF3 propeptide will bind to the cognate type I receptor but fail to bind the type II receptor, as type II receptor binding will be blocked by the associated propeptide portion. Accordingly, such a peptide will block signaling by endogenous GDF3 and may interfere with signaling by other TGF-beta family members that share the same Type I receptor.

In certain embodiments, the human GDF3 propeptide sequence may be altered to eliminate one or more cysteine residues. Preferably the final sequence will have an even number of cysteines. Three cysteines that may, in particular, be altered are underlined in FIG. 1. Of these, the cysteine in the sequence "RCS", which is not apparently conserved in the mouse sequence, will preferably be altered. Alternation may include deletion or replacement with a non-cysteine amino acid. In a preferred embodiment, the sequence alteration is designed, possibly in coordination with other sequence alterations to provide a glycosylation site.

In certain embodiments, the present invention contemplates specific mutations of the GDF3 propeptide sequences so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which is specifically recognized by appropriate cellular glycosylation enzymes. The alteration may also be made by the addition of, or substitution by, one or more serine or threonine residues to the sequence of the wild-type GDF3 propeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a GDF3 propeptide is by chemical or enzymatic coupling of glycosides to the GDF3 propeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on a GDF3 propeptide may be accomplished chemically and/or enzymatically. Chemical deglycosylation may involve, for 10 example, exposure of the GDF3 propeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on GDF3 propeptides can be achieved by the use of a variety of endo- and exo-glycosidases as described by Thotakura et al. (1987) Meth. Enzymol. 138: 350. The sequence of a propeptide may be adjusted, as appropriate, depending on the type of expression system used, as mammalian, yeast, insect and plant cells may all introduce differing glycosylation patterns that can be affected by the amino acid sequence of the peptide.

This disclosure further contemplates a method of generating mutants, particularly sets of combinatorial mutants of the GDF3 propeptide, as well as truncation mutants; pools of combinatorial mutants are especially useful for identifying functional variant sequences. The purpose of screening such combinatorial libraries may be to generate, for example, GDF3 propeptide variants which can act as either agonists or antagonist, or alternatively, which possess novel activities all together. A variety of screening assays are provided below, and such assays may be used to evaluate variants. For example, a GDF3 propeptide variant may be screened for its ability to bind to a GDF3 mature polypeptide or for the ability to prevent binding of a GDF3 mature polypeptide to a cell expressing a GDF3 receptor, such as an activin type II receptor or a type I receptor.

In certain embodiments, the activity of a GDF3 propeptide or its variants may also be tested in a cell-based or in vivo assay. For example, the effect of a GDF3 propeptide variant on adipogenesis (e.g., adipocyte proliferation and differentiation) in an adipocyte or precursor cell may be assessed. This may, as needed, be performed in the presence of recombinant GDF3, and cells may be transfected so as to produce GDF3, and the subject GDF3 propeptide variant. Likewise, a GDF3 propeptide may be administered to a mouse or other animal (e.g., the db/db obese mice), and one or more properties, such as fat cell number, size or proliferation rate may be assessed. The body mass index (BMI) or another estimate of body fat content may also be evaluated.

As another example, the effect of a GDF3 propeptide variant on the expression of genes involved in bone production in an osteoblast or precursor may be assessed. This may, as needed, be performed in the presence of recombinant GDF3, and cells may be transfected so as to produce GDF3, and the subject GDF3 propeptide variant. Likewise, a GDF3 propeptide may be administered to a mouse or other animal, and one or more bone properties, such as density or volume may be assessed. The healing rate for bone fractures may also be evaluated.

Combinatorially-derived variants can be generated which have a selective potency relative to a naturally occurring GDF3 propeptide. Such variant proteins, when expressed from recombinant DNA constructs, can be used in gene therapy protocols. Likewise, mutagenesis can give rise to variants which have intracellular half-lives dramatically different than the corresponding wild-type propeptide. For example, the altered protein can be rendered either more stable or less stable to proteolytic degradation or other cellular process which result in destruction of, or otherwise inactivation of a native GDF3 propeptide. Such variants, and the genes which encode them, can be utilized to alter GDF3 propeptide levels by modulating the half-life of the propeptide. For instance, a short half-life can give rise to more transient biological effects and, when part of an inducible expression system, can allow tighter control of recombinant GDF3 propeptide levels within the cell.

In a preferred embodiment, the combinatorial library is produced by way of a degenerate library of genes encoding a library of polypeptides which each include at least a portion of potential GDF3 propeptide sequences. For instance, a mixture of synthetic oligonucleotides can be enzymatically ligated into gene sequences such that the degenerate set of potential GDF3 propeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, GDF3 propeptide variants (both agonist and antagonist forms) can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137: 109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193: 653-660; Brown et al., (1992) Mol. Cell. Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of GDF3 propeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of GDF3 propeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, the GDF3 propeptides of the present invention include peptidomimetics. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the GDF3 propeptides.

To illustrate, by employing scanning mutagenesis to map the amino acid residues of a GDF3 propeptide which are involved in binding to another protein, peptidomimetic compounds can be generated which mimic those residues involved in binding. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), β-turn dipeptide cores (Nagai et al., (1985) Tetrahedron Lett 26:647; and Sato et al., (1986) J Chem Soc Perkin Trans 1:1231), and b-aminoalcohols (Gordon et al., (1985) Biochem Biophys Res Commun 126:419; and Dann et al., (1986) Biochem Biophys Res Commun 134:71).

In certain embodiments, the GDF3 propeptides of the invention may further comprise post-translational modifications in addition to any that are naturally present in the propeptide. Such modifications include, but are not limited to, acetylation, carboxylation, glycosylation, phosphorylation, lipidation, and acylation. As a result, the modified GDF3 propeptides may contain non-amino acid elements, such as polyethylene glycols, lipids, poly- or mono-saccharide, and phosphates. Effects of such non-amino acid elements on the functionality of a GDF3 propeptide may be tested as described herein for other GDF3 propeptide variants. When a GDF3 propeptide is produced in cells by cleaving a nascent form of the GDF3 protein, post-translational processing may also be important for correct folding and/or function of the protein. Different cells (such as CHO, HeLa, MDCK, 293, W138, NIH-3T3 or HEK293) have specific cellular machinery and characteristic mechanisms for such post-translational activities and may be chosen to ensure the correct modification and processing of the GDF3 protein into a GDF3 propeptide.

In certain aspects, functional variants or modified forms of the GDF3 propeptides include fusion proteins having at least a portion of the GDF3 propeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners. As another example, a fusion domain may be selected so as to facilitate detection of the GDF3 propeptide. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, a GDF3 propeptide is fused with a domain that stabilizes the propeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

In certain embodiments, the GDF3 propeptides of the present invention contain one or more modifications that are capable of stabilizing the GDF3 propeptides. For example, such modifications enhance the in vitro half life of the propeptides, enhance circulatory half life of the propeptides or reducing proteolytic degradation of the propeptides. Such stabilizing modifications include, but are not limited to, fusion proteins (including, for example, fusion proteins comprising a GDF3 propeptide and a stabilizer domain), modifications of a glycosylation site (including, for example, addition of a glycosylation site to a GDF3 propeptide), and modifications of carbohydrate moiety (including, for example, removal of carbohydrate moieties from a GDF3 propeptide). In the case of fusion proteins, a GDF3 propeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

It is understood that different elements of the fusion proteins may be arranged in any manner that is consistent with the desired functionality. For example, a GDF3 propeptide may be placed C-terminal to a heterologous domain, or, alternatively, a heterologous domain may be placed C-terminal to a GDF3 propeptide. The propeptide domain and the heterologous domain need not be adjacent in a fusion protein, and additional domains or amino acid sequences may be included C- or N-terminal to either domain or between the domains. In a preferred embodiment, the Fc portion will be positioned C-terminal to the propeptide.

A GDF3 propeptide fusion protein or coupled protein system (e.g. non-fusion covalent linkage by crosslinking) may also include a second inhibitor domain, which is a polypeptide affinity reagent that selectively binds to a GDF3 type I receptor. Such receptor may, for example, be one of ALK1, ALK2, ALK3, ALK4, ALK5, ALK6 or ALK7. The affinity reagent may be an antibody agent. An antibody agent may be, for example, a recombinant antibody; a monoclonal antibody; a VH domain; a VL domain; an scFv; an Fab fragment; an Fab' fragment; an F(ab')2; an Fv; or a disulfide linked Fv, a fully human antibody or a humanized chimeric antibody, or an antigen binding fragment thereof. An affinity reagent may also comprise a peptide or scaffolded peptide that selectively binds to GDF3 and competes with the binding of an ALK receptor. An affinity reagent may include a GDF3 binding domain of a cognate ALK receptor. For example, an extracellular domain of an ALK receptor (preferably human) may be used. The affinity reagent may be a small organic molecule that selectively binds to GDF3 and competes with the binding of an ALK receptor.

While one may readily identify soluble, extracellular portions of ALK receptors, tow examples are provided here. An example of a human ALK7 ligand binding domain is shown below:

LKCVCLLCDSSNFTCQTEGACWASVMLT-
NGKEQVIKSCVSLPELNAQVFCHSSN NVTKTECCFT-
DFCNNITLHLP (SEQ ID NO:9)

An example of a human ALK4 ligand binding domain is shown below:

ALLCACTSCLQANYTCETDGACM-
VSIFNLDGMEHHVRTCIPKVELVPAGK PFYCLSSEDL-
RNTHCCYTDY (SEQ ID NO:10)

In certain embodiments, the present invention makes available isolated and/or purified forms of the GDF3 propeptides, which are isolated from, or otherwise substantially free of, other proteins.

In certain embodiments, GDF3 propeptides (unmodified or modified) of the invention can be produced by a variety of art-known techniques. For example, such GDF3 propeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the GDF3 propeptides, fragments or variants thereof may be recombinantly produced using various expression systems (e.g., *E. coli*, Chinese Hamster Ovary cells, COS cells, baculovirus) as is well known in the art (also see below). In a further embodiment, the modified or unmodified GDF3 propeptides may be produced by digestion of naturally occurring or recombinantly produced GDF3 by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such GDF3 propeptides may be produced from naturally occurring or recombinantly produced GDF3 such as standard techniques known in the art, such as by chemical cleavage (e.g., cyanogen bromide, hydroxylamine).

In certain embodiments, the present invention contemplates making mutations in the proteolytic cleavage site of the GDF3 sequence to make the site less susceptible to proteolytic cleavage. The result is a GDF3 polypeptide containing both propeptide and mature portion, which may be useful as an antagonist of GDF3. More preferably, the mature portion is engineered with a stop codon, such that the GDF3 propeptide is produced with some portion of the mature peptide attached. In one specific embodiment, a mutant may contain a point mutation at amino acid 247, 248, 249 or 250 of SEQ ID NO: 3. In another specific embodiment, such mutant may contain a point mutation at amino acid 249, 250, 251 or 252 of SEQ ID NO: 4.

3. Nucleic Acids Encoding GDF3 Propeptides

In certain aspects, the invention provides isolated and/or recombinant nucleic acids encoding any of the GDF3 propeptides, including functional variants, disclosed herein. For example, SEQ ID NOs: 5 and 6 encode GDF3 propeptides. The subject nucleic acids may be single-stranded or double stranded. Such nucleic acids may be DNA or RNA molecules. These nucleic acids are may be used, for example, in methods for making GDF3 propeptides or as direct therapeutic agents (e.g., in a gene therapy approach).

The subject nucleic acids encoding GDF3 propeptides are further understood to include nucleic acids that are variants of SEQ ID NOs: 5 and 6. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NOs: 5 and 6.

In certain embodiments, the invention provides isolated or recombinant nucleic acid sequences that are at least 80%, 85%, 90%, 95%, 97%, 98%, 99% or 100% identical to SEQ ID NO: 5 or 6. One of ordinary skill in the art will appreciate that nucleic acid sequences complementary to SEQ ID NO: 5 or 6, and variants of SEQ ID NO: 5 or 6 are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 5 or 6, complement sequence of SEQ ID NO: 5 or 6, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 5-6 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding a GDF3 propeptide and operably linked to at least one regulatory sequence. Regulatory sequences are art-recognized and are selected to direct expression of the GDF3 propeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a GDF3 propeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant GDF3 propeptides include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of a subject GDF3 propeptide in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject GDF3 propeptide in cells propagated in culture, e.g., to produce proteins, including fusion proteins or variant proteins, for purification.

This invention also pertains to a host cell transfected with a recombinant gene including a coding sequence (e.g., SEQ ID NO: 5 or 6) for one or more of the subject GDF3 propeptides. The host cell may be any prokaryotic or eukaryotic cell. For example, a GDF3 propeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject GDF3 propeptides. For example, a host cell transfected with an expression vector encoding a GDF3 propeptide can be cultured under appropriate conditions to allow expression of the GDF3 propeptide to occur. The GDF3 propeptide may be secreted and isolated from a mixture of cells and medium containing the propeptide. Alternatively, the propeptide may be retained cytoplasmically or in a membrane fraction and the cells harvested, lysed and the protein isolated. A cell culture includes host cells, media and other byproducts. Suitable media for cell culture are well known in the art. The propeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the propeptide. In a preferred embodiment, the GDF3 propeptide is a fusion protein containing a domain which facilitates its purification.

In another embodiment, a fusion gene coding for a purification leader sequence, such as a poly-(His)/enterokinase cleavage site sequence at the N-terminus of the desired portion of the recombinant GDF3 propeptide, can allow purification of the expressed fusion protein by affinity chromatography using a $Ni^{2+}$ metal resin. The purification leader sequence can then be subsequently removed by treatment with enterokinase to provide the purified GDF3 propeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Antibodies

Another aspect of the invention pertains to antibodies. In certain embodiments, the present invention relates to an antibody that is specifically reactive with a GDF3 peptide which includes a mature GDF3 peptide and a GDF3 propeptide. Optionally, these subject antibodies bind competitively to mature GDF3 peptide and may be used as an antagonist of GDF3 activity. For example, the antibody may compete with GDF3 propeptide for binding to the mature GDF3. Such an antibody is expected to interfere with binding of GDF3 to its cognate Type II receptors. For example, by using immunogens derived from a GDF3 mature peptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the GDF3 peptide, an antigenic fragment which is capable of eliciting an antibody response, or a fusion protein. In a preferred embodiment, the inoculated mouse does not express endogenous GDF3, thus facilitating the isolation of antibodies that would otherwise be eliminated as anti-self antibodies. Techniques for conferring immunogenicity on a protein or peptide include conjugation to carriers or other techniques well known in the art. An immunogenic portion of a GDF3 peptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of a GDF3, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with GDF3 and monoclonal antibodies isolated from a culture comprising such hybridoma cells.

The term "antibody" as used herein is intended to include fragments thereof which are also specifically reactive with a subject GDF3 peptide. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. Fragments of antibodies may also be obtained by recombinant techniques; for example, variable domains of an antibody may be amplified by PCR, expressed as independent domains and assessed for antigen binding. The antibody of the present invention is further intended to include bispecific, single-chain, and chimeric and humanized molecules having affinity for a GDF3 peptide conferred by at least one CDR region of the antibody. In preferred embodiments, the antibody further comprises a label attached thereto and able to be detected (e.g., the label can be a radioisotope, fluorescent compound, enzyme or enzyme co-factor).

In certain preferred embodiments, an antibody of the invention is a monoclonal antibody, and in certain embodiments, the invention makes available methods for generating novel antibodies. For example, a method for generating a monoclonal antibody that binds specifically to a GDF3 peptide may comprise administering to a mouse an amount of an immunogenic composition comprising the GDF3 peptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the GDF3 peptide. Once obtained, a hybridoma can be propagated in a cell culture, optionally in culture conditions where the hybridoma-derived cells produce the monoclonal antibody that binds specifically to the GDF3 peptide. The monoclonal antibody may be purified from the cell culture.

The adjective "specifically reactive with" as used in reference to an antibody is intended to mean, as is generally understood in the art, that the antibody is sufficiently selective between the antigen of interest (e.g., a GDF3 peptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore binding assay, Bia-core AB, Uppsala, Sweden), sandwich assays (e.g., the paramagnetic bead system of IGEN International, Inc., Gaithersburg, Md.), western blots, immunoprecipitation assays, and immunohistochemistry.

In certain specific aspects, the disclosure provides antibodies that bind to a GDF3 propeptide. Such antibodies may be generated much as described above, using a propeptide or fragment thereof as an antigen. Antibodies of this type can be used, e.g., to detect GDF3 propeptides in biological samples and/or to monitor GDF3 propeptide levels in an individual. The level of GDF3 propeptides maybe measured in a variety of sample types such as, for example, in cells, and/or in bodily fluid, such as in whole blood samples, blood serum, blood plasma and urine. In certain cases, an antibody that specifically binds to a GDF3 propeptide can be used to stimulate activity of GDF3, thereby stimulating the growth of tissues such as adipose tissue.

5. Screening Assays

In certain aspects, the present invention relates to the use of a GDF3 peptide (including a GDF3 mature peptide and a GDF3 propeptide) to identify compounds (agents) which are agonist or antagonists of a GDF3 mature peptide. Compounds identified through this screening can be tested in tissues such as fat, bone, cartilage, or muscle, to assess their ability to modulate tissue growth in vitro. Optionally, these compounds can further be tested in animal models to assess their ability to modulate tissue growth in vivo.

There are numerous approaches to screening for therapeutic agents for modulating bone/cartilage growth by targeting a GDF3 peptide. In certain embodiments, high-throughput screening of compounds can be carried out to identify agents that perturb a GDF3 peptide-mediated effects on adipose tissue growth (e.g., adipocyte growth or proliferation) or other tissues, such as bone, cartilage or muscle. In one embodiment, the assay is used to identify compounds that specifically modulate (increase or decrease) expression or activity of a GDF3 peptide. In another embodiment, the compounds can be identified by their ability to interact with a GDF3 peptide (e.g., a GDF3 mature peptide or a GDF3 propeptide). In yet another embodiment, the assay is carried out to screen and identify compounds that specifically reduce or increase binding of a GDF3 peptide to its binding partner.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of adipocyte growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a GDF3 peptide and its binding protein.

Merely to illustrate, in an exemplary screening assay of the present invention, the compound of interest is contacted with an isolated and purified GDF3 propeptide which is ordinarily capable of binding to a GDF3 mature peptide, as appropriate for the intention of the assay. To the mixture of the compound and GDF3 propeptide is then added a composition containing a GDF3 mature peptide. Detection and quantification of GDF3 propeptide complexes provides a means for determining the compound's efficacy at inhibiting (or potentiating) complex formation between the GDF3 propeptide and its binding protein. The efficacy of the compound can be assessed by generating dose response curves from data obtained using various concentrations of the test compound. Moreover, a control assay can also be performed to provide a baseline for comparison. For example, in a control assay, isolated and purified GDF3 mature peptide is added to a composition containing the GDF3 propeptide, and the formation of GDF3 propeptide/mature peptide complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the GDF3 propeptide and its binding protein may be detected by a variety of techniques. For instance, modulation of the formation of complexes can be quantitated using, for example, detectably labeled proteins such as radiolabelled (e.g., $^{32}P$, $^{35}S$, $^{14}C$ or $^{3}H$), fluorescently labeled (e.g., FITC), or enzymatically labeled GDF3 propeptide or its binding protein, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between a GDF3 propeptide and its binding protein. Further, other modes of detection such as those based on optical waveguides (PCT Publication WO 96/26432 and U.S. Pat. No. 5,677,196), surface plasmon resonance (SPR), surface charge sensors, and surface force sensors are compatible with many embodiments of the invention.

Moreover, the present invention contemplates the use of an interaction trap assay, also known as the "two hybrid assay," for identifying agents that disrupt or potentiate interaction between a GDF3 peptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interaction between a GDF3 peptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; 5,965,368.

In one specific example, interaction between a GDF3 propeptide and a GDF3 mature peptide can be assayed by making a construct which expresses a FLAG-tagged GDF3 precursor protein. The FLAG-tagged precursor protein is expressed in cells and processed into a GDF3 propeptide and a FLAG-tagged mature peptide. The protein lysates prepared from the cells are then affinity-purified by antibodies against FLAG. Complexes containing a GDF3 propeptide and a GDF3 mature peptide can be determined by the presence of a GDF3 propeptide in these affinity-purified protein samples (e.g., by immunoblot).

In certain embodiments, the subject compounds are identified by their ability to interact with a GDF3 peptide (e.g., a GDF3 mature peptide or a GDF3 propeptide). The interaction between the compound and the GDF3 peptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to a GDF3 peptide. This may include a solid phase or fluid phase binding event. Alternatively, the gene encoding a GDF3 peptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for controlling weight gain and obesity. At the cellular level, adipocyte proliferation and differentiation, which leads to the generation of additional fat cells (adipocytes), is critical in the development of obesity. Therefore, any compound identified can be tested in whole cells or tissues, in vitro or in vivo, to confirm their ability to modulate adipogeneis by measuring adipocyte proliferation or differentiation. Various methods known in the art can be utilized for this purpose.

For example, the effect of a GDF3 peptide (e.g., a GDF3 mature peptide or a GDF3 propeptide) or test compounds on adipogenesis can be determined by measuring differentiation of 3T3-L1 preadipocytes to mature adipocytes in cell based assays, such as, by observing the accumulation of triacylglycerol in Oil Red O staining vesicles and by the appearance of certain adipocyte markers such as FABP (aP2/422) and PPARγ2. See, for example, Reusch et al., 2000, Mol Cell Biol. 20:1008-20; Deng et al., 2000, Endocrinology. 141:2370-6; Bell et al., 2000, Obes Res. 8:249-54. Another example of cell-based assays includes analyzing the role of GDF3 peptides and test compounds in proliferation of adipocytes or adipocyte precursor cells (e.g., 3T3-L1 cells), such as, by monitoring bromodeoxyuridine (BrdU)-positive cells. See, for example, Pico et al., 1998, Mol Cell Biochem. 189:1-7; Masuno et al., 2003, Toxicol Sci. 75:314-20.

The present invention also contemplates in vivo assays to measure adipogenesis and body weight gain. For example, Witthuhn et al., Cytokine, 14:129-135 (2001) discloses upregulation of GDF3 expression in adipose tissue of FABP/aP2 null mice which develop obesity. Therefore, the subjective compounds can be tested in the FABP/aP2 null mice to see if they regulate adipocyte proliferation or differentiation in vivo. Alternatively, the subject compounds can be assayed in the FABP/aP2 null mice for their ability to reduce or prevent obesity. Other animal models for obesity studies, such as ob/ob and db/db mice, and Zucker fatty (fa/fa) rat, can be used similarly for the same purpose. See, for example, Grasa et al., 2000, Horm Metab Res. 32:246-50; Zhang et al., 1996, J Biol Chem. 271:9455-9. These references are incorporated by reference herein in their entirety for their disclosure of using animal models for study on obesity and obesity-related disorders.

In certain aspects, the present invention provides methods and agents for controlling abnormal cell growth and differentiation, and disorders related thereto, in particular tumor growth. Thus, any compound identified can be tested in whole cells or tissues, in vitro or in vivo, to confirm their ability to inhibit cell growth (proliferation) or differentiation. Preferred cells are tumor cells, such as testicular germ cell tumor cells (Clark, et al., 2004, Stem Cells 22:169-79; Caricasole et al., 1998, Oncogene 16:95-103). Methods for evaluating anti-tumor activity of a compound are well known and routine in the art. See, for example, Harstrick et al., 1989, Cancer. 63:1079-83; Sun et al., 2004, Anticancer Res. 24:179-86.

In other aspects, the present invention provides methods and agents for stimulating bone formation and increasing bone mass. Therefore, any compound identified can be tested in whole cells or tissues, in vitro or in vivo, to confirm their ability to modulate bone or cartilage growth. Various methods known in the art can be utilized for this purpose.

For example, the effect of a GDF3 peptide (e.g., a GDF3 mature peptide or a GDF3 propeptide) or test compounds on bone or cartilage growth can be determined by measuring induction of Msx2 or differentiation of osteoprogenitor cells into osteoblasts in cell based assays (see, e.g., Daluiski et al., Nat Genet. 2001, 27(1):84-8; Hino et al., Front Biosci. 2004, 9:1520-9). Another example of cell-based assays includes analyzing the osteogenic activity of the GDF3 peptides and test compounds in mesenchymal progenitor and osteoblastic cells. To illustrate, recombinant adenoviruses expressing a human GDF3 propeptide were constructed to infect pluripotent mesenchymal progenitor C3H10T1/2 cells, preosteoblastic C2C12 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8): 1544-52).

The present invention also contemplates in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. These references are incorporated by reference herein in their entirety for their disclosure of rat model for study on osteoporotic bone fracture. In certain aspects, the present invention makes use of fracture healing assays that are known in the art. These assays include fracture technique, histological analysis, and biomechanical analysis, which are described in, for example, U.S. Pat. No. No. 6,521,750, which is incorporated by reference in its entirety for its disclosure of experimental protocols for causing as well as measuring the extent of fractures, and the repair process.

It is understood that the screening assays of the present invention apply to not only the subject GDF3 propeptides and variants of the GDF3 propeptides, but also any test compounds including agonists and antagonist of a GDF3 protein. Further, these screening assays are useful for drug target verification and quality control purposes.

6. Exemplary Therapeutic Uses

In certain aspects, compositions (e.g., GDF3 propeptides) of the present invention can be used for treating or preventing a disease or condition that is associated with abnormal activity of GDF3. These diseases, disorders, or conditions are generally referred to herein as "GDF3-associated disorders," which are described in detail below. In certain embodiments, the present invention provides methods of treating or preventing an individual in need thereof through administering to the individual a therapeutically effective amount of a GDF3 propeptide as described above. These methods are particularly aimed at therapeutic and prophylactic treatments of animals, and more particularly, humans.

In certain embodiments, the present invention provides compositions and methods for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present invention relates to regulating body weight by administering to an animal a GDF3 propeptide. As discussed above, inhibitors of GDF-3 will tend to inhibit increases in body fat content in response to overeating, and particularly in response to a high fat diet.

In one specific embodiment, the present invention relates to methods and compounds for reducing body weight and/or reducing weight gain in an animal, and more particularly, for treating or ameliorating obesity in patients at risk for or suffering from obesity. In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass. In the former embodiment, the method comprises administering to an animal a GDF3 antagonist compound, such as GDF3 propeptides (both naturally-occurring peptides and homologues or mimetics thereof). In the latter embodiment, the methods comprise administering to an animal that is at risk for developing or has low body weight and/or a detrimental condition related thereto, a GDF3 agonist compound, such as a GDF3 mature peptide or a homologue (mimetic) thereof, and an antibody specific for GDF3 propeptide.

As used herein, the phrase "GDF3 agonist compound" or "GDF3 agonist" refers to any fragment, homologue or mimetic (peptide or non-peptide) of a GDF3 mature peptide (e.g., a naturally occurring or prototype) which is characterized by its ability to agonize (e.g., stimulate, induce, increase, enhance) the biological activity of the naturally occurring GDF3 mature peptide (e.g., interaction/binding with and/or activation of a GDF3 receptor). The phrase "GDF3 antagonist compound" or "GDF3 antagonist" refers to any fragment, homologue or mimetic (peptide or non-peptide) of a GDF3 mature peptide (e.g., naturally occurring or prototype) which is characterized by its ability to antagonize (e.g., inhibit, block, decrease, compete against) the biological activity of the naturally-occurring GDF3 mature peptide (e.g., interaction/binding with and/or activation of a GDF3 receptor). Terms used herein in connection with GDF3 genes and proteins (e.g., "compound," "analog," "homologue," and "mimetic") are also described in detail above. In one embodiment of the present invention, a GDF3 compound is an isolated nucleic acid molecule that encodes a GDF3 peptide, a peptide analog thereof, or a fusion protein comprising such a peptide. In addition, nucleic acid molecules useful in the present invention may include antisense nucleic acids and double-stranded small interfering RNAs (siRNAs) that inhibit or reduce GDF3 gene expression.

In certain embodiments, the compounds of the invention are administered in an amount effective to induce a measurable decrease or increase in the body weight and/or mass of the animal, or minimally, to increase the rate of gain or reduce the rate of loss of body weight and/or mass in the animal. Optionally, the subject compounds can be administered in conjunction with one or more other compounds that are useful for regulating body weight and/or mass, and particularly, for decreasing or increasing body weight in an animal. Preferably, decreasing or increasing body weight and/or mass and/or increasing or reducing the rate of weight and/or mass loss/gain in an animal is effective for treating or ameliorating undesired health-compromising conditions associated with low or high body weight, such conditions being discussed below.

According to the present invention, "undesirable" gain of body weight and/or mass refers to any gain of body weight or body mass (e.g., gain of body mass can occur in the absence of measurable or significant weight gain) in an individual, as compared to a prior weight or body mass of that individual, where such weight and/or mass gain is unintended, unexpected, and/or unhealthy, as determined by the individual or by a medical professional evaluating such individual. Similarly, "unhealthy" or "health-compromising" weight and/or mass gain is referred to herein as any gain of body weight or body mass which is either deemed by the individual or medical professional to be unhealthy, or which results in a symptom that can be associated with poor health, such as diabetes or cardiovascular conditions. Accordingly, "undesirable" loss of body weight and/or mass refers to any loss of body weight or body mass (e.g., loss of body mass can occur in the absence of measurable or significant weight gain) in an individual, as compared to a prior weight or body mass of that individual, where such weight and/or mass loss is unintended, unexpected, and/or unhealthy, as determined by the individual or by a medical professional evaluating such individual. Similarly, "unhealthy" or "health-compromising" weight and/or mass loss is referred to herein as any loss of body weight or body mass which is either deemed by the individual or medical professional to be unhealthy, or which results in a symptom that can be associated with poor health, such as heart problems, weakened immune function, lack of strength or energy, and/or depression.

In certain embodiments, methods and compounds of the present invention are useful for treating any condition or disorder that is characterized by or associated with undesirable or unhealthy body weight or body mass gain or loss. With regard to undesirable or unhealthy body weight or body mass gain, such conditions include, but are not limited to, non-insulin dependent diabetes mellitus (NIDDM), cardiovascular disease, cancer, hypertension, osteoarthritis, stroke, respiratory problems, and gall bladder disease. Other conditions associated with undesirable or unhealthy body weight or body mass gain, such conditions include, but are not limited to depression, mood disorders, reproductive dysfunction, and pharmaceutical non-compliance. With regard to undesirable or unhealthy body weight or body mass loss, such conditions, include, but are not limited to, wasting syndromes (e.g., wasting disease, cachexia and sarcopenia) and conditions associated with such syndromes, including, but not limited to, aging, cancer, AIDS (or HIV infection), extensive surgery, chronic infections, immunologic diseases, hyperthyroidism, extraintestinal Crohn's disease, psychogenic disease, chronic heart failure or other severe trauma. According to the present invention, the phrase "wasting syndrome" is used generally to refer to any condition characterized by undesirable weight and/or body mass loss. The term "cachexia" is used to refer to a metabolic and sometimes, eating disorder, which is additionally characterized by hypermetabolism and hypercatabolism, and which results in a loss of fat-free mass, and particularly, body cell mass. "Sarcopenia" refers to another such disorder which is typically characterized by loss of muscle mass. The term "wasting disease" is used to more specifically refer to loss of body weight, including both the fat and the fat-free compartments, which is typically found in the elderly, or in late stage cachexia or sarcopenia.

In one specific embodiment, methods and compounds of the present invention are particularly useful for treating obesity. As used herein, the terms "obese" and "obesity" refer to a condition in which an animal (typically human) has a body mass index (BMI) of greater than 27 kilograms per square meter. The phrase, "to treat obesity" in a patient refers to reducing, ameliorating or preventing obesity in a patient that suffers from obesity or is at risk of becoming obese. Preferably, the disorder (e.g., obesity), or the potential for developing the disorder, is reduced, optimally, to an extent that the patient no longer suffers from or does not develop the disorder (e.g., excessive accumulation of fat stores in adipose tissue), or the discomfort and/or altered functions and detrimental conditions associated with such disorder. More particularly, "to control" or "to regulate" body weight, or specifically "to treat obesity," includes the administration of the subject compounds as disclosed herein to prevent the onset of the symptoms or complications of undesired body weight, to alleviate the symptoms or complications, or to eliminate the disorder. Treating obese patients, for example, may include, but is not limited to, lowering body weight and/or decreasing the rate of weight gain. Individuals having a BMI equal to or less than 27 kilograms per square meter, while not considered to be obese according to the present invention, can also be treated using the method of the present invention to reduce body weight, for example, for cosmetic purposes, athletic training purposes, or for health-associated purposes. The present invention is also useful for treating individuals (e.g., patients) with a percent body fat greater than 20%, and preferably, greater than about 25%, and more preferably, greater than about 30%, and even more preferably, greater than about 35%, 40%, and 45%, in increasing preference. It is to be noted that certain individuals, such as certain athletes, can actually have a BMI greater than 27 kilograms per square meter, while having a relatively low or healthy percent body fat, and therefore, one of skill in the art will appreciate that such individuals may not actually be considered to be obese. On the other hand, the present invention is useful for treating patients having undesirable low body weight by administration of GDF3 agonists.

In the methods of the present invention, therapeutic compositions can be administered to any animal, and preferably, to any member of the vertebrate class (e.g., mammals), including without limitation, primates, rodents, livestock, and domestic pets. Livestock include mammals to be consumed or that produce useful products (e.g., sheep for wool production). Preferred mammals to treat include humans. According to the present invention, the term "patient," "individual" or "subject" is used to describe both human and non-human animals. In a preferred embodiment, the present method is used for treating obese patients.

In certain embodiments, the present invention contemplates use of the subject compounds (e.g., GDF3 propeptides) in combination with other therapeutic modalities. Thus, in addition to the therapies described above, one may also provide to the patient other "standard" therapies for regulating body weight and for treating or preventing conditions related thereto. Examples of these standard therapies include, but are not limited to, melanocyte-stimulating hormone (MSH), leptin, anabolic steroids, growth hormones, erythropoietin, cytokines, and anti-cytokine agents. See e.g., U.S. Pat. No. 6,716,810. For example, these combinatorial therapies may be achieved with a single composition or pharmacological formulation that includes both agents, or with two distinct compositions or formulations, at the same time. Alternatively, one agent may precede or follow administration of the other agent by intervals ranging from minutes to weeks. In embodiments where two or more different kinds of therapeutic agents are applied separately to an individual, one would generally ensure that a significant period of time did not expire between the time of each delivery, such that these different kinds of agents would still be able to exert an advantageously combined effect on the target tissues or cells.

In one specific embodiment, the methods disclosed herein can also be used in conjunction with other methods related to the treatment of excess body weight or related conditions, including, but not limited to, co-administration of another body weight regulating compound (e.g., leptin), exercise, diet, or liposuction. For example, post-operative or post-dietetic administration of a therapeutic composition of the present invention could be used to reduce the reoccurrence of weight gain, to generally reduce adipose tissue in areas of the patient's body which were not treated.

In certain embodiments, the present invention provides compositions and methods for controlling abnormal cell growth and differentiation, and treating disorders related thereto, such as tumors. For example, human embryonal carcinoma and testicular germ cell tumors (TGCTs) can be therapeutic targets of the subject compounds. One embodiment of the present invention relates to treating or preventing tumors by administering to an animal a GDF3 propeptide.

Optionally, the subject compounds can be administered in conjunction with one or more other antitumor compounds in an animal. Exemplary antitumor compounds include, but are not limited to, aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

In a specific embodiment, the subject compounds can be combined with a compound selected from cisplatin, carboplatin, and iproplatin in treating germ cell tumors such as TGCTs.

In other embodiments, the present invention provides methods of inducing bone and/or cartilage formation, preventing bone loss, increasing bone mineralization or preventing the demineralization of bone. For example, the subject GDF3 propeptides and compounds identified in the present invention have application in treating osteoporosis and the healing of bone fractures and cartilage defects in humans and other animals. GDF3 propeptides may be useful in patients that are diagnosed with subclinical low bone density, as a protective measure against the development of osteoporosis.

In one specific embodiment, methods and compositions of the present invention may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent contributes to the repair of congenital, trauma-induced, or oncologic resection induced craniofacial defects, and also is useful in cosmetic plastic surgery. Further, methods and compositions of the invention may be used in the treatment of periodontal disease, and in other tooth repair processes. In certain cases, the subject GDF3 propeptides may provide an environment to attract bone-forming cells, stimulate growth of bone-forming cells or induce differentiation of progenitors of bone-forming cells. GDF3 propeptides of the invention may also be useful in the treatment of osteoporosis. Further, GDF3 propeptides may be used in cartilage defect repair and prevention/reversal of osteoarthritis.

In another specific embodiment, the invention provides a therapeutic method and composition for repairing fractures and other conditions related to cartilage and/or bone defects or periodontal diseases. The invention further provides therapeutic methods and compositions for wound healing and tissue repair. The types of wounds include, but are not limited to, burns, incisions and ulcers. See e.g., PCT Publication No. WO84/01106. Such compositions comprise a therapeutically effective amount of at least one of the GDF3 propeptide of the invention in admixture with a pharmaceutically acceptable vehicle, carrier or matrix.

In another specific embodiments, methods and compositions (e.g., GDF3 propeptides) of the invention can be applied to conditions causing bone loss such as osteoporosis, hyperparathyroidism, Cushing's disease, thyrotoxicosis, chronic diarrheal state or malabsorption, renal tubular acidosis, or anorexia nervosa. Many people know that being female, having a low body weight, and leading a sedentary lifestyle are risk factors for osteoporosis (loss of bone mineral density, leading to fracture risk). However, osteoporosis can also result from the long-term use of certain medications. Osteoporosis resulting from drugs or another medical condition is known as secondary osteoporosis. In a condition known as Cushing's disease, the excess amount of cortisol produced by the body results in osteoporosis and fractures.

The most common medications associated with secondary osteoporosis are the corticosteroids, a class of drugs that act like cortisol, a hormone produced naturally by the adrenal glands. Although adequate levels of thyroid hormones (which are produced by the thyroid gland) are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenyloin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anticlotting medication; and cholestyramine (Questran) and colestipol (Colestid), used to treat high cholesterol. Gum disease causes bone loss because these harmful bacteria in our mouths force our bodies to defend against them. The bacteria produce toxins and enzymes under the gum-line, causing a chronic infection.

In other embodiments, the present invention provides methods and therapeutic agents, for example, antagonists of GDF3 propeptides, for treating diseases or disorders associated with abnormal or unwanted bone growth. For example, patients having the disease known as Fibrodysplasia Ossificans Progressiva (FOP) grow an abnormal "second skeleton" that prevents any movement. Additionally, abnormal bone growth can occur after hip replacement surgery and thus ruin the surgical outcome. This is a more common example of pathological bone growth and a situation in which antagonists of GDF3 propeptides may be therapeutically useful. Antagonists of GDF3 propeptides may also be useful for treating other forms of abnormal bone growth, such as the pathological growth of bone following trauma, burns or spinal cord injury. In addition, antagonists of GDF3 propeptides may be useful for treating or preventing the undesirable conditions associated with the abnormal bone growth seen in connection with metastatic prostate cancer or osteosarcoma. Examples of these antagonists of GDF3 propeptides include, but are not limited to, compounds that disrupt interaction between a GDF3 propeptide and its binding partner (e.g., a GDF3 mature peptide) and antibodies that specifically bind to a GDF3 propeptide.

7. Pharmaceutical Compositions

In certain embodiments, compounds (e.g., GDF3 propeptides or GDF3 antibodies) of the present invention are formulated with a pharmaceutically acceptable carrier. For example, a subject compound of the invention can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to the tissue site, such as fat, bone, cartilage or tissue damage. For example, topical administration may be suitable for wound healing and tissue repair. Therapeutically useful agents other than the subject compounds which may also optionally be included in the composition as described above, may alternatively or additionally, be administered simultaneously or sequentially with a subject compound in the methods of the invention. Preferably for bone and/or cartilage formation, the composition would include a matrix capable of delivering a subject compound (e.g., a GDF3 propeptide) or other therapeutic compounds to the site of bone and/or cartilage damage, providing a structure for the developing bone and cartilage and optimally capable of being resorbed into the body. For example, the matrix may provide slow release of the subject compounds. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the invention (e.g., a GDF3 propeptide), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenteral administration may comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., a GDF3 propeptide). The various factors include, but are not limited to, amount of bone weight desired to be formed, the site of bone damage, the condition of the damaged bone, the size of a wound, type of damaged tissue, the patient's age, sex, and diet, the severity of any infection, time of administration, and other clinical factors. Optionally, the dosage may vary with the type of matrix used in the reconstitution and the types of compounds in the composition. The addition of other known growth factors to the final composition, may also effect the dosage. Progress can be monitored by periodic assessment of bone growth and/or repair, for example, X-rays, histomorphometric determinations, and tetracycline labeling.

In certain embodiments, one or more compounds of the invention can be administered, together (simultaneously) or at different times (sequentially or overlapping). In addition, the subject compounds can be administered with another type of therapeutic agents, for example, a body weight-reducing agent, a cartilage-inducing agent, a bone-inducing agent or a muscle-inducing agent. The two types of compounds may be administered simultaneously or at different times. It is expected that the subject compounds of the invention may act in concert with or perhaps synergistically with another therapeutic agent.

For example, a variety of osteogenic, cartilage-inducing and bone-inducing factors have been described, particularly bisphosphonates. See e.g., European Patent Application Nos. 148,155 and 169,016. For example, other factors that can be combined with the subject GDF3 propeptides include various growth factors such as epidermal growth factor (EGF), platelet derived growth factor (PDGF), transforming growth factors (TGF-α and TGF-β), and insulin-like growth factor (IGF). Agents (compounds) for regulating body weight and for treating body weight associated disorders are described above.

In certain embodiments, the present invention also provides gene therapy for the in vivo production of GDF3 protein. In one embodiment, such gene therapy would achieve its therapeutic effect by introduction of a polynucleotide which encodes a GDF3 peptide (e.g., a GDF3 mature peptide or a GDF3 propeptide) into cells or tissues having the disorders as listed above. In another embodiment, such gene therapy would achieve its therapeutic effect by introduction of nucleic acids that inhibit gene expression of GDF3, such as GDF3 antisense probes and double-stranded small interfering RNAs (siRNAs). Methods of making and using antisense nucleic acids and siRNAs are known in the art. See, for example, Crooke, 2004, Annu Rev Med. 55:61-95; Schutze, 2004, Mol Cell Endocrinol. 213(2):115-9, and articles referenced therein.

In certain embodiments, delivery of the nucleic acids for gene therapy can be achieved using a recombinant expression vector such as a chimeric virus or a colloidal dispersion system. Preferred for therapeutic delivery of these polynucleotides is the use of targeted liposomes.

Various viral vectors which can be utilized for gene therapy as taught herein include adenovirus, adeno-associated virus (AAV), herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector encoding a GDF3 peptide. In one preferred embodiment, the vector is targeted to fat, bone, cartilage or muscle cells/tissues.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for the subject nucleic acids is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., 1981, Trends Biochem. Sci., 6:77). Methods for efficient gene transfer using a liposome vehicle, are known in the art (see e.g., Mannino, et al., 1988, Biotechniques, 6:682). The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXAMPLES

The invention now being generally described, it will be more readily understood by reference to the following examples, which are included merely for purposes of illustration of certain embodiments and embodiments of the present invention, and are not intended to limit the invention.

Example 1

Construction, Expression, and Purification of GDF3 pro-Fc Fusion

A human GDF3 propeptide sequence was PCR amplified from a full length GDF3 cDNA and cloned into a human CMV derived expression vector in such a way that upon ligation it gave a fusion peptide with a murine IgG2a Fc domain. This construct was transiently transfected in HEK293 cells using polyethylenimine (PEI). After seven days, cells were harvested and conditioned media was collected for purification.

Recombinant GDF3pro-Fc fusion was expressed in HEK293 cells and purified by standard techniques. For example, the protein can be purified as follows. Recombinant GDF3 pro-MuIgG2a fusion is purified by protein A affinity chromatography. 1 liter batch of conditioned media is filtrated, concentrated and loaded on a 4 ml rProtein A Sepharose Fast Flow column (Amersham Biosciences) previously equilibrated with TBS (pH 8.0). After protein loading, the column is washed with 20 column volumes (CV) of TBS, 10 CV of TBS-0.05% Tween 20, followed by additional wash with 10 CV of TBS to remove non-specifically bound proteins. Bound GDF3 pro-MuIgG2a protein is eluted with 100 mM Glycine (pH 3.0). Eluted fraction is immediately neutralized by addition of 1 M Tris and dialyzed against PBS (pH 8.0).

Example 2

GDF3 pro-Fc Fusion Peptide Binds to Mature GDF3

BiaCore chip analysis was conducted. Purified GDF3 pro-Fc was coupled onto a BiaCore CM5 chip using the amine coupling procedure. Conditioned medium from cells expressing human GDF-3 was injected onto the chip and binding was detected, as shown in the upper trace in FIG. 9. In a control experiment, conditioned medium from cells that do not express GDF3 was injected onto the chip and little or no binding was detected, as shown in the lower trace in FIG. 9.

Incorporation by Reference

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

---

We claim:

1. An isolated monoclonal antibody that binds to a mature GDF3 peptide and competes with GDF3 propeptide for binding to the mature GDF3 peptide.

2. The antibody of claim 1, wherein the mature GDF3 peptide consists of the sequence of amino acids 251-364 of SEQ ID NO: 3.

3. The antibody of claim 1, wherein the antibody is a humanized or fully human antibody.

4. A pharmaceutical preparation comprising an antibody of claim 1.

* * * * *